US008354440B2

(12) United States Patent
Halperin et al.

(10) Patent No.: US 8,354,440 B2
(45) Date of Patent: Jan. 15, 2013

(54) 3-3-DI-SUBSTITUTED-OXINDOLES AS INHIBITORS OF TRANSLATION INITIATION

(75) Inventors: José A. Halperin, Brookline, MA (US); Amarnath Natarajan, Texas City, TX (US); Bertal Huseyin Aktas, Newton, MA (US); Yun-Hua Fan, San Antonio, TX (US); Han Chen, College Station, TX (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 13/233,074

(22) Filed: Sep. 15, 2011

(65) Prior Publication Data

US 2012/0077759 A1 Mar. 29, 2012

Related U.S. Application Data

(60) Continuation of application No. 12/916,956, filed on Nov. 1, 2010, now Pat. No. 8,044,089, which is a continuation of application No. 12/368,588, filed on Feb. 10, 2009, now Pat. No. 7,846,962, which is a division of application No. 11/463,421, filed on Aug. 9, 2006, now Pat. No. 7,737,172, which is a continuation of application No. PCT/US2005/004373, filed on Feb. 11, 2005.

(60) Provisional application No. 60/544,384, filed on Feb. 13, 2004.

(51) Int. Cl.
*A61K 31/427* (2006.01)
*A61K 31/4178* (2006.01)
*A61K 31/404* (2006.01)

(52) U.S. Cl. ......... 514/369; 514/397; 514/414; 514/418

(58) Field of Classification Search .................. 514/418, 514/397, 369, 414
See application file for complete search history.

(56) References Cited

U.S. PATENT DOCUMENTS

| 4,053,483 A | 10/1977 | Hosta Pujol et al. |
| 4,522,811 A | 6/1985 | Eppstein et al. |
| 5,849,780 A | 12/1998 | Di Malta et al. |
| 5,914,431 A | 6/1999 | Fennhoff |
| 2007/0299102 A1 | 12/2007 | Felding et al. |

FOREIGN PATENT DOCUMENTS

| DE | 2521966 C3 | 11/1975 |
| DE | 19638888 A1 | 3/1998 |
| DE | 10202874 A1 | 8/2003 |
| DK | 200400576 | 4/2004 |
| DK | 200400693 | 5/2004 |
| DK | 2004701153 | 7/2004 |
| DK | 200401216 | 8/2004 |
| JP | 50154242 | 12/1975 |
| JP | 7301916 A | 11/1995 |
| JP | 8183853 A | 7/1996 |
| JP | 2002179649 A | 6/2002 |
| JP | 2002179650 A | 6/2002 |
| JP | 2003176269 A | 6/2003 |
| RU | 1823440 A1 | 11/1996 |
| WO | 03078394 A1 | 9/2003 |
| WO | 2005097107 A2 | 10/2005 |
| WO | 2006083869 A2 | 8/2006 |
| WO | 2006083970 A2 | 8/2006 |
| WO | 2008071387 A1 | 6/2008 |
| WO | 2008129075 A1 | 10/2008 |

OTHER PUBLICATIONS

Communication pursuant to Article 94(3) EPC corresponding to EP Application No. 05 722 960.1-1211, issued Jun. 13, 2012.
Bolotov, V.V., et al., "Synthesis and Antiinflammatory Activity of some 3, 3-Diphenyl-2-Oxoindoline Carboxylic Acids and their Amides," Translated from Khimiko-Farmatsevticheskii Zhurnal, Feb. 18, 1980, pp. 39-42, vol. 14, Plenum Publishing Corporation.
Barker, Marvin W., et al., "Oxindoles from α-Acyloxyamides," J. Heterocyclic, Jan. 24, 1977, pp. 521-522, vol. 14, Department of Chemistry, Mississippi State University, Mississippi.
Examiner's Report relating to corresponding CA Application No. 2,555,812, issued Mar. 6, 2012.
English Abstract of JP2002179649; Jun. 26, 2002; Tsujigami, et al.
English Abstract of JP2002179650; Jun. 26, 2002; Tsujigami, et al.
English Abstract of JP2003176269; Jun. 24, 2003; Ashimori, et al.
Watkins, et al., Translation Initiation and Its Deregulation During Tumorigenesis, journal, Feb. 28, 2002, 1023-1027, 86 (7), Bristish Journal of Cancer, UK.
Wang, et al., Expression of the Eukaryotic Translation Initiation Factors 4E and 2a Correlates with the Progression of Thyroid Carcinoma, abstract and presentation platform; Mar. 1999, 1101-1107, vol. 11, No. 12, MaryAnn Liebert, Inc., San Francisco.
Wang, et al., Expression of Eukaryotic Translation Initiation Factors 4e and 2a in Non-Hodgkin's Lymphomas, journal, Jul. 1999, 247-255, vol. 155 No. 1, American Journal of Pathology, US.
Rosenwald, The Role of Translation in Neoplastic Transformation From a Pathologist's Point of View, journal, 2004, 3230-3247, Nature Publishing Group, Albuquerque, NM.
Rosenwald, et al., Expression of Translation Initiation Factor eIF-2a is Increased in Benign and Malignant Melancitytic and Colonic Epithelial Neoplasms, journal, Sep. 1, 2003, 1080-1088, vol. 98. No. 5, American Cancer Society.
Meric, et al., Translation Initiation in Cancer: A Novel Target for Therapy, journal, Sep. 2002, 971-979, vol. 1, Houston, TX.
Marintchev, et al., Topology and Regulation of the Human EIF4A/4G/4H Helicase Complex in Translation Initiation, Feb. 6, 2009, 1-14, Elsevier, Inc.

(Continued)

*Primary Examiner* — Kristin Bianchi
(74) *Attorney, Agent, or Firm* — Banner & Witcoff, Ltd.

(57) ABSTRACT

Compositions and methods for inhibiting translation using 3-(5-tert-Butyl-2-Hydroxy-phenyl)-3-phenyl-1,3-dihydro-indol-2-one and/or its derivatives are provided. Compositions, methods and kits for treating (1) cellular proliferative disorders, (2) non-proliferative, degenerative disorders, (3) viral infections, and/or (4) disorders associated with viral infections, using 3-(5-tert-butyl-2-hydroxy-phenyl)-3-phenyl-1,3-dihydro-indol-2-one and/or its derivatives are described.

4 Claims, 8 Drawing Sheets

(4 of 8 Drawing Sheet(s) Filed in Color)

OTHER PUBLICATIONS

Natarajan, et al., Journal of Medicinal Chemistry, journal, Oct. 7, 2004, 4978-4981, vol. 47 No. 21, American Chemical Society, Cambridge, MA.

Bilanges, et al., Mechanisms of Translation Deregulation in Human Tumors and Therapeutic Intervention Strategies, journal, Apr. 2, 2007, 5973-5990, USF Cancer Research, San Fransico, CA.

International Preliminary Report on Patentability relating to PCT/US2005/004373, filed Feb. 11, 2005.

Shoichet et al., Structure-Based Discovery of Inhibitors of Thymidylate Synthase, Mar. 5, 1993, Science, vol. 259, 1445-1450.

Lala, et al., Cancer and Metastasis reviews (1998), 17 (1), 91-106.

Aktas, et al., "Depletion of Intracellular Ca2+Stores, Phosphorylation of eIF2alpha, and sustained inhibitionof translation initiation mediate the anticancer effects of clotrimazole," Proc. Natl. Acad. Sci. USA 195: 8280-8285 (1998).

Benzaquen, et al., "Clotrimazole inhibits cell proliferation in vitro and in vivo," Nature Medicine, 1:534-540 (1995).

Bodanszky, et al., "formation of the Peptide Bond," Peptide Synthesis, Chapter 5, pp. 85-128. John Wiley & Sons. New York (1976).

Hewawasam, et al., "The Synthesis and Characterization of BMS-204352 (MaxiPost™) and Related 3-Flourooxindoles as Openers of Maxi-K Potassium Channels." Bioorganic & Medicinal Chemistry Letters, 12:1023-1026 (2002).

Klumpp et al., "Preparation of 3, 3-Diaryloxindoles by Superacid-Induced Condsations of Isatins and Anomatics with a Combinatorial Approach," J. Org. Chem., 63:4481-4484 (1998).

Kozak J., "An Analysis of Vertebrate mRNA Sequences: Intimations of Translational Control," Cell. Biol., 115:887-903 (1991).

Kozak, "Initiation of Translation in Prokaryotes and Eukaryotes," Gene, 234:187-208 (1999).

Kozak, "Deteminants of Translational Fidelity and Efficiency in Vertebrate mRNAs," Biochimie, 76:815-821 (1994).

Miyawaki, et al., "Cameleons as Cytosolie and Intra-Organellar Calcium Probes," Oxford University Press:Oxford, London;pp. 3-16 (2001).

Pain, "Initiation of Protein Synthesis in Eukaryotic Cells," Eur. J. Biochem., 236-747-771 (1996).

Palakurthi, et al., "Inhibition of Translation Initiation Mediates the Anticancer Effect of the n-3 Polyunsaturated Fatty Acid Eicosapentaenoic Acid," Cancer Research, 60:2919-2925 (2000).

Palakurthi, et al., "Anticancer Effects of Thiazolidinediones Are Independent of Peroxisome Prolferator-Activated Receptor γ . . . ," Cancer Research, 61: 6213-6218 (2001).

Stewart and Young, Solid Phase Peptide Synthesis, pp. 31-34 and 71-82, Pierce Chemical Company, Rockford, IL 1984.

Moerke, et al., "Small-Molecule Inhibition of the Interaction between the Translation Initiation Factors eIF4E and eIF4G," Cell, vol. 28, pp. 257-267 (2007).

Golub, et al., "Molecular Classification of Cancer: Class Discovery and Class Prediction by Gene Expression Monitoring," Science, 286: 531-537 (1999).

Supplementary Partial European Search Report Corresponding to EP 05722960.1 filed Aug. 11, 2006.

Chemical Abstract of Bolotov, V.V., et al., "Synthesis and Antiinflammatory Activity of 3,3-diphenyl-2-oxoindolecarboxylic Acids and Their Amides," 1980; XP002540991.

Chemical Abstract of Petyunin, P.A., et al., "Chemistry of Heterocycles.XXXI. Synthesis of 3,3-di-aryloxindoles and 1-methyl-3-oxo-4, 4-Diphenyltetra hydroisoquinoline Based on Arylamides of Diphenylchloroacetic and Diphenylakoxyacetic Acids," 1957; XP002540992.

Chemical Abstract of Shklyaev, V.S., et al., "Reactivity of Compounds with a Diarylmethylol Group XVIII. Cyclization Kinetics of Substituted Anilides of di-p-tolylglycolic and Benzilic Acids" 1972; XP002540993.

Chemical Abstract of Barker, Marvin W, et al., "Oxindoles From. alpha.-acyloxyamides" 1977; XP002540994.

Chemical Abstract of Petyunin, P.A., et al., "Chemistry of Heterocycles. LIII Case of Deamination During the Acidochromic Cyclization if Arylamides of Diarylglycolic Acids," 1972; XP00254995.

Chemical Abstract of Petyunin, P.A., et al., "Chemistry of Heterocycles. L. Aminoalkylation or 3,3-disubstituted Oxindoles" 1973; XP00254996.

Chemical Abstract of Bolotov, V.V., et al., "Synthesis and Anti-inflammatory Activity of 3, 3-disubstituted 2-oxoindoline-1-acetic Acids and Their Derivatives," 1979; XP002540997.

Chemical Abstract of Ogata, Masaru, et al., "Synthesis and Antimycotic Properties of 3-(1-imidazolyl) indolin-2-ones," 1981; XP002540998.

Natarajan, Amarnath, et al., "3, 3-Diaryl-1, 3-dihydroindol-2-ones as Antiproliferatives Mediated by Translation Initiation Inhibition," j. Med. Chem. 2004, 47, 1882-1885; XP002347248.

English Translation of Rejection Notice relating to corresponding JP Application No. 2006-553263, issued Dec. 2, 2010.

English Abstract of JP Application No. 50-154242, 1976.

Barker, M., et al., "Oxindoles from α-Acyloxyamides," J. Heterocyclic Chem., 14, 521 (1977).

Ogata, M., et al., "Synthesis and Antimycotic Properties of 3-(1-Imidazolyl)Indolin-2-Ones," Eur, J. Med. Chem.-Therapeutica, Jul.-Aug. 6, 1981, No. 4, pp. 373-379.

Examination Report relating to corresponding AU Application No. 2005214338, issued May 3, 2010.

Examination Report relating to corresponding AU Application No. 2005214338, issued Jun. 17, 2011.

Examination Report relating to corresponding CA Application No. 2,555,812, issued Aug. 4, 2011.

English Translation of Rejection Notice relating to corresponding JP Application No. 2006-553263, issued Aug. 24, 2011.

| AA1 ↓ | Met | Pro | Asn | Ala | Asp |
|---|---|---|---|---|---|
| Leu | ✓ | ✓ | ✓ | n.d. | ✓ |
| Phe | ✓ | ✓ | ✗ | ✓ | ✗ |

| AA1 ↓ | Phe | Thr |
|---|---|---|
| Ala | ✓ | ✓ |
| Gln | ✓ | ✓ |
| Leu | ✓ | ✓ |
| Phe | ✓ | ✓ |
| Trp | ✓ | ✓ |

| AA1 ↓ | Met | Pro | Asn | Ala | Asp |
|---|---|---|---|---|---|
| Leu | ✓ | ✓ | ✓ | ✓ | ✓ |
| Phe | ✓ | ✓ | ✗ | ✓ | ✓ |

| AA1 ↓ | Phe | Thr |
|---|---|---|
| Ala | ✓ | ✓ |
| Gln | ✓ | ✓ |
| Leu | ✓ | ✓ |
| Phe | ✓ | ✓ |
| Trp | ✓ | ✓ |

# 3-3-DI-SUBSTITUTED-OXINDOLES AS INHIBITORS OF TRANSLATION INITIATION

RELATED U.S. APPLICATION(S)

This application is a continuation of U.S. patent application Ser. No. 12/916,956, filed Nov. 1, 2010 which is a continuation of U.S. patent application Ser. No. 12/368,588, filed Feb. 10, 2009, now U.S. Pat. No. 7,846,962 which is a divisional of U.S. patent application Ser. No. 11/463,421, filed Aug. 9, 2006, now U.S. Pat. No. 7,737,172 which is a continuation of PCT application no. PCT/US2005/004373, designating the United States and filed Feb. 11, 2005 which claims the benefit of the filing date of U.S. provisional application No. 60/544,384, filed Feb. 13, 2004; each of which is hereby incorporated herein by reference in its entirety.

STATEMENT OF GOVERNMENT INTERESTS

This invention was made with Government support under Grant Number 5 U19 CA87427 awarded by the National Institutes of Health. The Government has certain rights in the invention.

FIELD OF THE INVENTION

The present invention relates to novel compounds which inhibit translation initiation, pharmaceutical compositions of the novel compounds, and methods of treating medical disorders.

BACKGROUND OF THE INVENTION

Translation, the mRNA-directed synthesis of proteins, occurs in three distinct steps: initiation, elongation and termination. Translation initiation is a complex process in which the two ribosomal subunits and methionyl tRNA (met-tRNA) assemble on a properly aligned mRNA to commence chain elongation at the AUG initiation codon. The established scanning mechanism for initiation involves the formation of a ternary complex among eukaryotic initiation factor 2 (eIF2), GTP and met-tRNA. The ternary complex recruits the 40S ribosomal subunit to form the 43S pre-initiation complex. This complex recruits mRNA in cooperation with other initiation factors such as eukaryotic initiation factor 4E (eIF4E), which recognizes the 7-methyl-guanidine cap (m-$^7$GTP cap) in an mRNA molecule and forms the 48S pre-initiation complex. Cap recognition facilitates the 43S complex entry at the 5' end of a capped mRNA. Subsequently, this complex migrates linearly until it reaches the first AUG codon, where a 60S ribosomal subunit joins the complex, and the first peptide bond is formed (Pain (1996) *Eur. J. Biochem.*, 236: 747-771).

Several features of the mRNA structure influence the efficiency of its translation. These include the m-$^7$GTP cap, the primary sequence surrounding the AUG codon and the length and secondary structure of the 5' untranslated region (5' UTR). Indeed, a moderately long, unstructured 5' UTR with a low G and C base content seems to be optimal to ensure high translational efficiency. Surprisingly, sequence analysis of a large number of vertebrate cDNAs has shown that although most transcripts have features that ensure translational fidelity, many do not appear to be designed for efficient translation (Kozak (1991) *J. Cell. Biol.*, 115:887-903). Many vertebrate mRNAs contain 5' UTRs that are hundreds of nucleotides long with a remarkably high GC content, indicating that they are highly structured because G and C bases tend to form highly stable bonds. Because highly structured and stable 5' UTRs are the major barrier to translation, mRNAs with stable secondary structure in their 5' UTR are translated inefficiently and their translation is highly dependent on the activity of translation initiation factors.

mRNAs with complex, highly structured 5' UTRs include a disproportionately high number of proto-oncogenes such as the G1 cyclins, transcription and growth factors, cytokines and other critical regulatory proteins. In contrast, mRNAs that encode globins, albumins, histones and other housekeeping proteins rarely have highly structured, GC-rich 5' UTRs (Kozak (1994) *Biochimie*, 76; 815-21; Kozak (1999) *Gene*, 234:187-208). The fact that genes encoding for regulatory but not for housekeeping proteins frequently produce transcripts with highly structured 5' UTRs indicates that extensive control of the expression of regulatory genes occurs at the level of translation. In other words, low efficiency of translation is a control mechanism which modulates the yield of proteins such as cyclins, mos, c-myc, VEGF, TNF, among others, that could be harmful if overproduced.

SUMMARY

Translation initiation is a critical step in the regulation of cell growth because the expression of most oncogenes and cell growth regulatory proteins is translationally regulated. One approach to inhibiting translation initiation has recently been identified using small molecule known as translation initiation inhibitors. Without intending to be bound by theory, FIG. 1 sets forth a summary of the anti-cancer mechanism of action of translation initiation inhibitors such as clotrimazole (CLT) and the diaryloxindole (DAO) compounds of the present invention. CLT inhibits translation initiation by sustained depletion of intracellular Ca$^{2+}$ stores. Depletion of intracellular Ca$^{2+}$ stores activates "interferon-inducible" "double-stranded RNA activated" protein kinase (PKR) which phosphorylates and thereby inhibits the α subunit of eIF2. Since the activity of eIF2 is required for translation initiation, its inhibition by compounds such as CLT reduces the overall rate of protein synthesis. Because most cell regulatory proteins are encoded for by mRNAs containing highly structured 5' UTRs, they are poorly translated and their translation depends heavily on translation initiation factors such as eIF2 and eIF4. Therefore, inhibition of translation initiation preferentially affects the synthesis and expression of growth regulatory proteins such as G1 cyclins. Sequential synthesis and expression of G1 cyclins (D1, E and A) is necessary to drive the cell cycle beyond the restriction point in late G1. Thus, the decreased synthesis and expression of G1 cyclins resulting from CLT-induced inhibition of translation initiation causes cell cycle arrest in G1 and inhibits cancer cell and tumor growth (Aktas et al. (1998) *Proc. Natl. Acad. Sci. USA*, 95:8280-8285, incorporated herein by reference in its entirety for all purposes).

Like CLT, the n-3 polyunsaturated fatty acid eicosapentaenoic acid (EPA) depletes internal calcium stores, and exhibits anti-carcinogenic activity. Unlike CLT, however, EPA is a ligand of peroxisome proliferator-activated receptor gamma (PPARγ), a fatty acid-activated transcription factor. Although EPA and other ligands of PPARγ, such as troglitazone and ciglitazone, inhibit cell proliferation, they do so in a PPARγ-independent manner (Palakurthi et al. (2000) *Cancer Research*, 60:2919; and Palakurthi et al. (2001) *Cancer Research*, 61:6213, incorporated herein by reference in their entirety for all purposes).

Embodiments of the present invention are directed to compounds that inhibit translation initiation, and the use of such compounds for treating (1) proliferative disorders, (2) non-proliferative, degenerative disorders, (3) viral infections, and/or (4) disorders associated with viral infections are disclosed. Certain examples are directed to the use of a combination of the compounds described herein for treating (1) proliferative disorders, (2) non-proliferative, degenerative disorders, (3) viral infections, and/or (4) disorders associated with viral infections.

In at least certain examples, DAO compounds are provided. The terms "diaryloxindole" AND "DAO" are intended to include substituted diphenyloxindole compounds such as, for example, 3-(5-tert-butyl-2-hydroxy-phenyl)-3-phenyl-1,3-dihydro-indol-2-one-type compounds. In one example, diaryloxindole compounds of the present invention are set forth in Formula I. In certain examples, the diaryloxindole compounds of the present invention deplete intracellular calcium stores. In another example, diaryloxindole compounds are effective to inhibit translation initiation. In one aspect, the diaryloxindole compounds of the present invention include compounds comprising Formula I to Formula XIV, and/or the active and partially active compounds set forth in Tables 1-14 and FIGS. 4A-4B.

In accordance with a method aspect, a method of treating a proliferative disorder by providing and/or administering a diaryloxindole compound to a mammal, e.g., a human or a non-human (e.g., a non-human primate), is provided. In one example, the proliferative disorder is cancer. In accordance with other examples, a method of treating a viral infection by providing and/or administering a diaryloxindole compound to a mammal, e.g. a human or a non-human mammal, is provided.

In accordance with an additional aspect, kits are provided for the treatment of (1) proliferative disorders, (2) non-proliferative, degenerative disorders, (3) viral infections, and/or (4) disorders associated with viral infections. In one aspect, the kits comprise a diaryloxindole compound, a pharmaceutically acceptable carrier, and optionally, instructions for use. The pharmaceutical composition can be administered to a human subject or a non-human subject depending on the disorder to be treated.

It will be recognized by the person of ordinary skill in the art that the compounds, compositions, methods and kits disclosed herein provide significant advantages over prior technology. Compounds, compositions, methods and kits can be designed or selected to relieve and/or alleviate symptoms in a patient suffering from one or more disorders. These and other aspects and examples are described below.

BRIEF DESCRIPTION OF THE DRAWINGS

The patent or application file contains at least one drawing executed in color. Copies of this patent or patent application publication with color drawing(s) will be provided by the Office upon request and payment of the necessary fee. The foregoing and other features and advantages of the present invention will be more fully understood from the following detailed description of illustrative embodiments taken in conjunction with the accompanying drawings.

Figure 1:
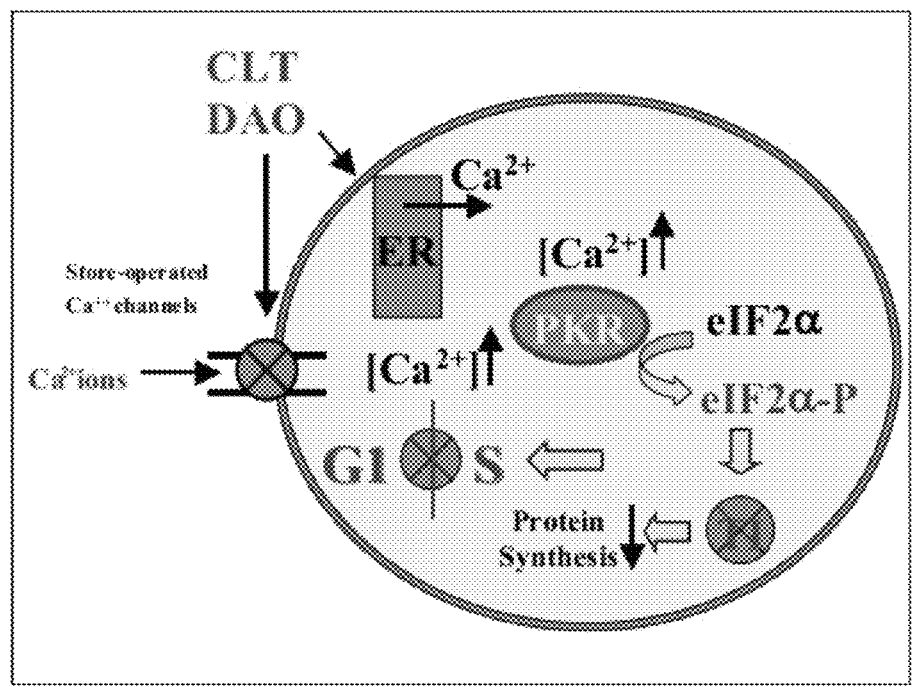
FIG. 1 depicts a schematic of the anti-cancer mechanism of action for translation initiation inhibitors such as clotrimazole (CLT) and diaryloxindole (DAO).
Figure 2:
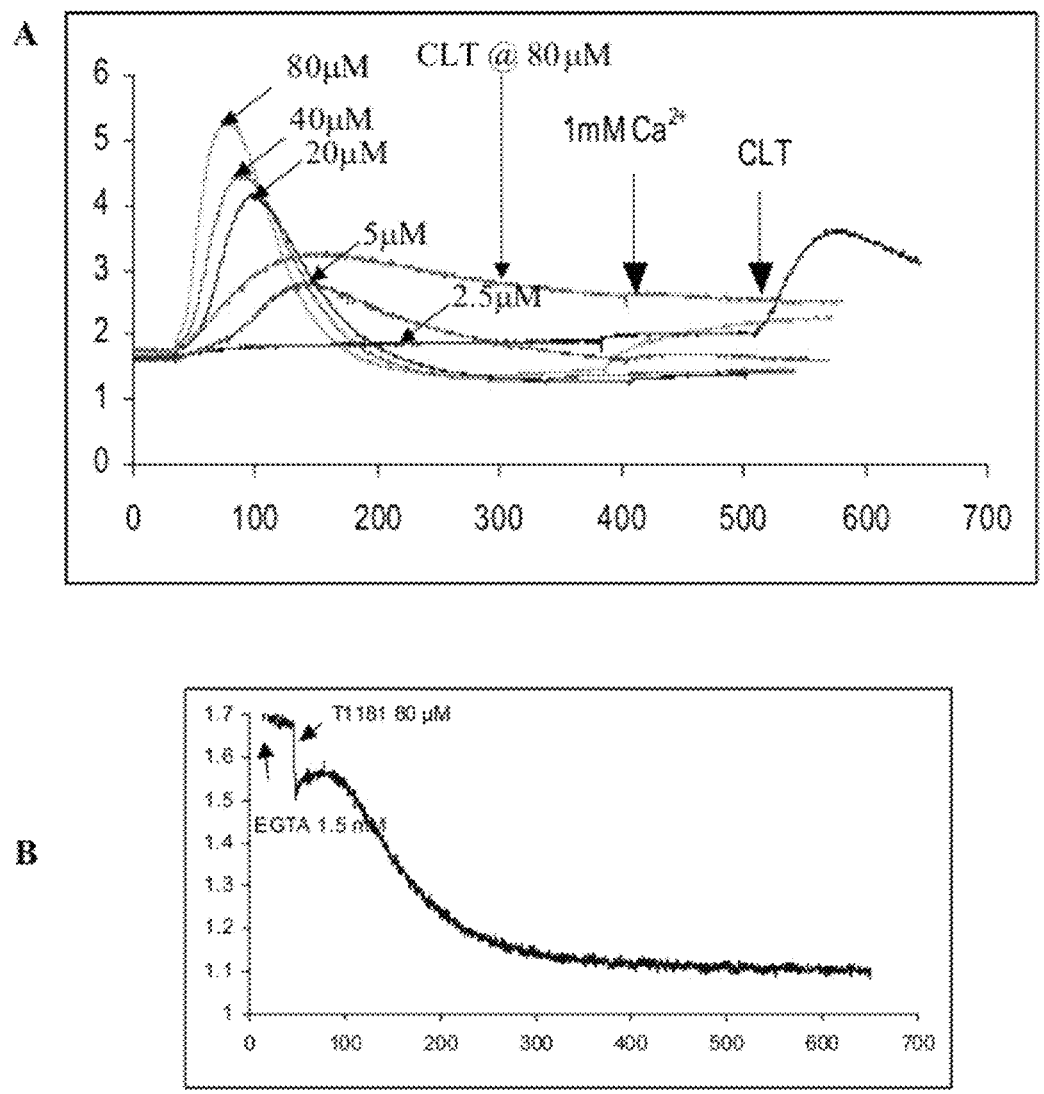
FIGS. 2A-2B depict compound 1181 activity. (A) depicts calcium ($Ca^{2+}$) release in a dose dependent manner as compared to CLT from intracellular stores measured using dye-loaded cells. (B) depicts depletion of endoplasmic reticulum (ER) $Ca^{2+}$ in stable cells lines carrying ER-targeted $Ca^{2+}$-sensitive chameleon proteins exposed to compound 1181, in accordance with certain examples. These proteins emit light and the $Ca^{2+}$ content is measured by fluorescent resonance energy transfer (FRET).
Figure 3:
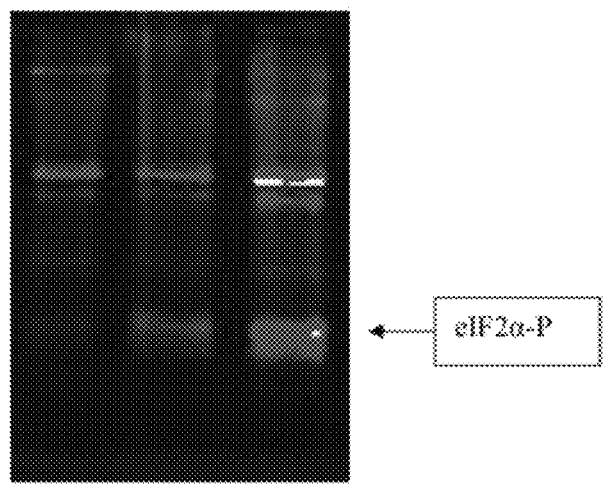
FIGS. 3A-3C depict compound 1181 activity. (A) depicts the drug induced phosphorylation of eIF2α protein in control (lane 1), positive control (lane 2) and 1181 (lane 3) measured using Western blot analysis. (B) shows the in vitro anti-cancer effect of 1181 in human lung cancer cells (A549) measured using sulfur rhodamine B (SRB) assay. (C) graphically depicts depletion of ternary complex in transgenic KLN cells exposed to compound 1181.
Figure 3:
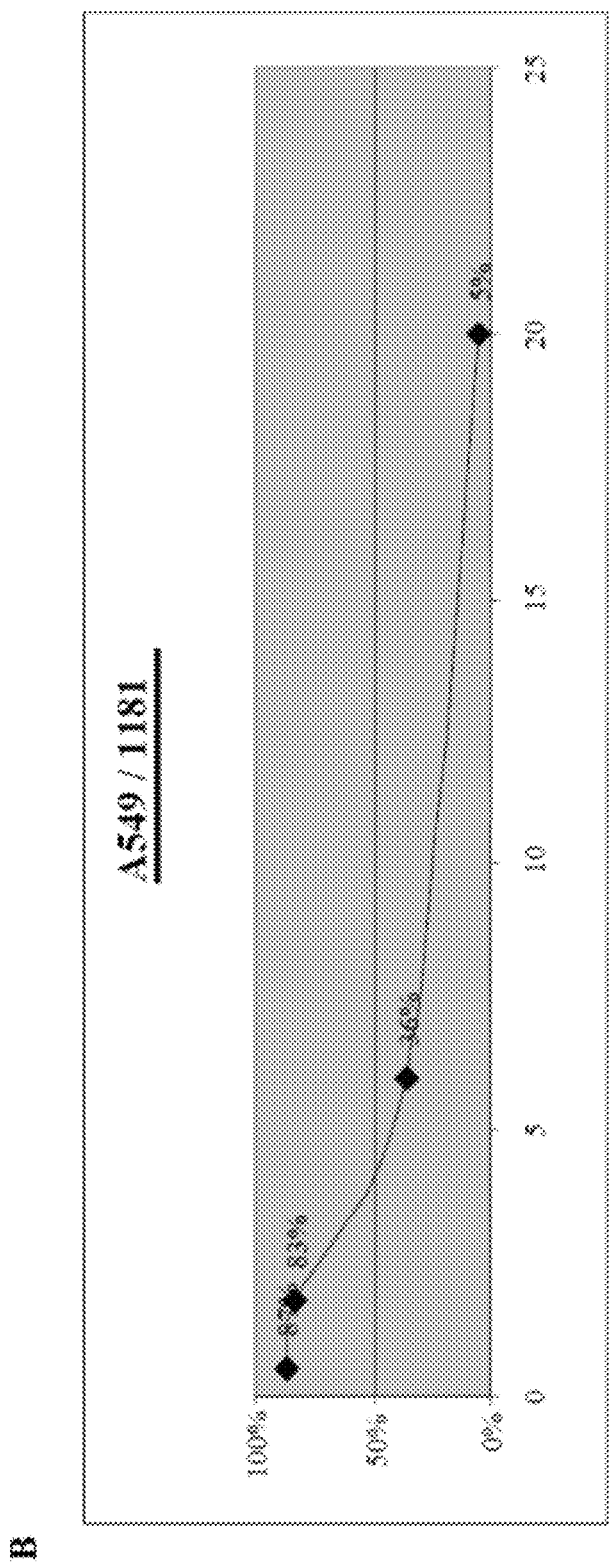
Figure 3:
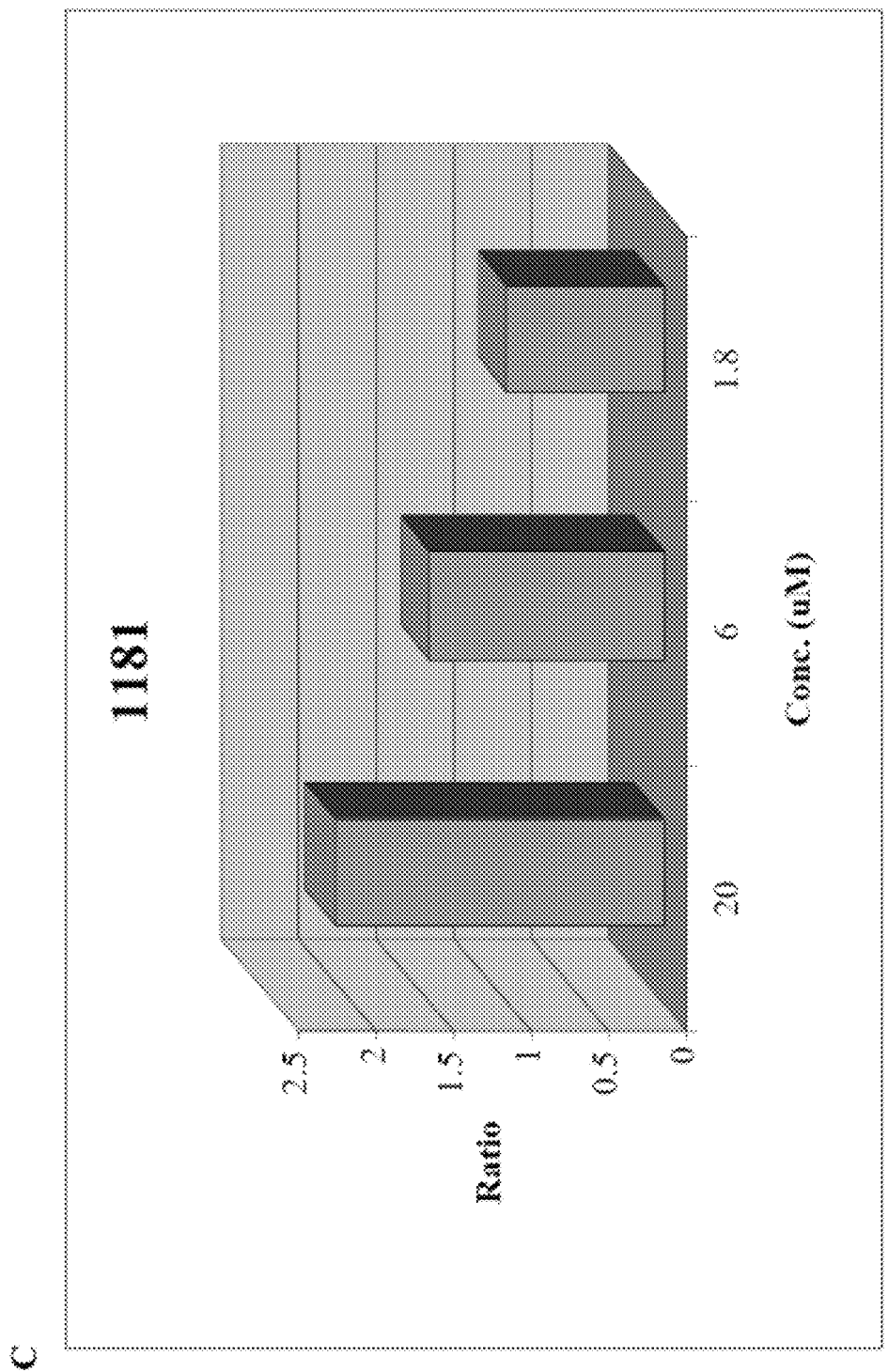

It will be recognized that the results and examples in the figures are only illustrative and other examples and illustrations will be readily recognized by the person of ordinary skill in the art, given the benefit of this disclosure.

DETAILED DESCRIPTION OF CERTAIN EMBODIMENTS

In accordance with certain examples, diaryloxindole compounds that inhibit translation (e.g., translation initiation) are provided. Such compounds are useful for the treatment of (1) proliferative disorders, (2) non-proliferative, degenerative disorders, (3) viral infections, and/or (4) disorders associated with viral infections.

Certain examples are described below with reference to various chemical formulae. The chemical formulae referred to herein can exhibit the phenomena of tautomerism, conformational isomerism, stereo isomerism or geometric isomerism. As the formulae drawings within this specification can represent only one of the possible tautomeric, conformational isomeric, enantiomeric or geometric isomeric forms, it should be understood that the invention encompasses any tautomeric, conformational isomeric, enantiomeric or geometric isomeric forms which exhibit biological or pharmacological activity as described herein.

The compounds and compositions provided below are effective to inhibit translation (e.g., translation initiation) at least to the extent necessary for effective treatment of one or more disorders described herein. While in certain examples translation may be substantially inhibited such that little or no activity results, in other examples the inhibition is at least sufficient to relieve and or alleviate the symptoms from a selected disorder to be treated.

In accordance with certain embodiments, compounds of the invention are represented by the generic formula set forth below.

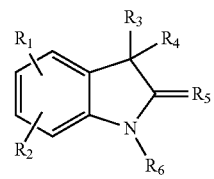

In accordance with certain aspects, $R_1$ is selected from the group consisting of (halo)alky, (un)substituted (alkyl)aryl, halogen, CN, COOH, alkenyl, alkynyl, alkoxy, cycloalkoxy, H, 2-OH, 2-Me, 2-OMe, 2-$CH_2CO_2H$, 2-NHFmoc, 2-$NHSO_2CH_2Ph$ (wherein Ph is phenyl), 2-$NHSO_2CH_3$, 2-$NHSO_2$(4-tBu)Ph, 2-$NHSO_2$(4-NHAc)Ph, 2-$NHSO_2$(3-$CF_3$)Ph, 2-$NHSO_2$(4-$NO_2$)Ph, 2-$NHSO_2$(4-OMe)Ph, 2-$NHSO_2$(4-Br)Ph, 2-$NHSO_2$(4-I)Ph, 2-$NHSO_2$(4-Ph)Ph, 2-$NHSO_2$(4-OPh)Ph, 2-NHAc, 2-NHCO(4-tBu)Ph, 3-O($CH_2$)$_4NMe_2$, 3-O($CH_2$)$_4N_3$, 3-t-Bu, 3-OMe, 3-Cl, 3-F, 3-Me, 3-t-Bu, 3'-NHSO₂(4-tBu)Ph, 4-Cl, 4-F, 4-Br, 4-OH, 4-Et, 4-O(CH₂)₃CHCH₂, 4-n-propyl, 4-i-Bu, 4-n-Bu, 4-O(CH₂)₂OH, 4-OMe, 4-t-Bu, 4-OPh, 4-Ph, 4-NMe₂, 4-ethyl, 5-Br, 5-Cl, 5-I, 5-sulfonic acid, 5-nitro, 5-ethyl, 5-fluoro, 5-OCF₃, 5-NO₂, 5-OMe, 5-NH₂, 5-Et, 5-F, 5-N₃, 5-NHSO₂-1-napthyl, 6-ethyl, 6-Br, H, 6-Et, 6-Cl, 7-ethyl, 7-COOH, 7-COOMe, 7-Br, 7-CF₃, 7-OMe, 7-I and 7-Et; $R_2$ is selected from the group consisting of (halo)alky, (un)substituted (alkyl)aryl, halogen, CN, COOH, alkenyl, alkynyl, alkoxy, cycloalkoxy, H, 2-Me and 2-OMe, 2-OH, 3-Cl, 3-F, 3-Me, 4-F, 4-O(CH₂)₃CHCH₂, 4-OH, 4-t-Bu, 4-O(CH₂)₃CHCH₂, 7-formamide-N-[2-(4-Amino-phenyl)-ethyl], 7-COOH, 7-CH₂OH and 7-CH₂-N-imidazole; $R_3$ is selected from the group consisting of (un)substituted aryl, (un)substituted heterocyclic, (un)substituted heteroaromatic, Ar—NHSO₂Ar, Ar—NHCOAr, H,

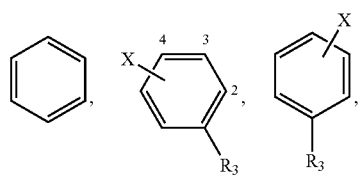

2-thiophene, —(CH₂)₁₁CH₃, —CH₂Ph, —CCH, -cyclohexyl and —C₆F₅, wherein X is selected from the group consisting of H, 2-OH, 2-OMe, 2-Me, 2-OMe, 2-OH, 2-CH₂CO₂H, 3-OMe, 3-Cl, 3-F, 3-Me, 3-O(CH₂)₄NMe₂, 3-O(CH₂)₄N₃, 3-t-Bu, 4-F, 4-O(CH₂)₃CHCH₂, 4-OH, 4-n-propyl, 4-i-Bu, 4-n-Bu, 4-O(CH₂)₂OH, 4-OMe, 4-t-Bu, 4-OMe, 4-OPh, 4-Ph, and 4-NMe₂; $R_4$ is selected from the group consisting of (un)substituted aryl, (un)substituted heterocyclic, (un)substituted heteroaromatic, Ar—NHSO₂Ar, Ar—NHCOAr, H,

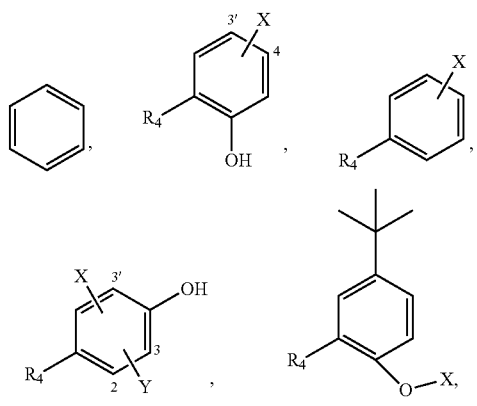

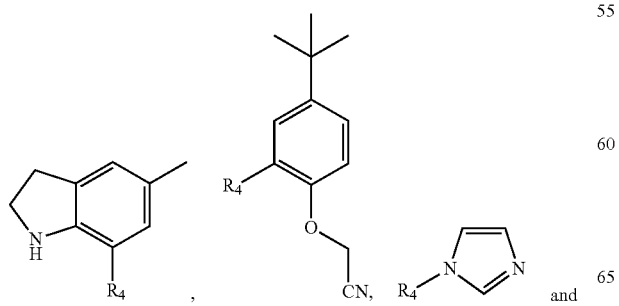

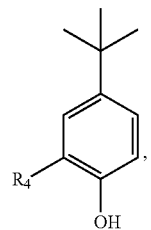

wherein X is selected from the group consisting of H, —SO₂-Camphor, —CO(CH₂)₆COOH, —CO(CH₂)₃CONHOH, —CH₂CH₂NHBoc, —CO(CH₂)₃COOH, —CH₂COOH, —CH₂CO-Leu-Phe-CH₂OH, —CH₂COOMe, 2-OH, 2-Me, 2-NHFmoc, 2-NHSO₂CH₂Ph, 2-NHSO₂CH₃, 2-NHSO₂(4-tBu)Ph, 2-NHSO₂(4-NHAc)Ph, 2-NHSO₂(3-CF₃)Ph, 2-NHSO₂(4-NO₂)Ph, 2-NHSO₂(4-OMe)Ph, 2-NHSO₂(4-Br)Ph, 2-NHSO₂(4-I)Ph, 2-NHSO₂(4-Ph)Ph, 2-NHSO₂(4-OPh)Ph, 2-NHAc, 2-NHCO(4-tBu)Ph, 3'-CH₂CH(CO₂Me)NH₂, 3'-CH₂CH(CO₂Me)NHFmoc, 3'-t-Bu, 3'-t-Bu, 3'-OH, 3'-O(CH₂)₃CHCH₂, 3'-O(CH₂)₄Br, 3'-O(CH₂)₄NMe₂, 3'-O(CH₂)₄N₃,

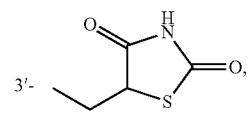

3'-O(CH₂)₄NH₂, 3'-CF₃, 3'-CH₃, 3'-n-heptyl, 3'-n-nonyl, 3'-i-Bu, 3'-i-Propyl, 3'-n-Propyl, 3'-n-Octyl, 3'-Et, 3'-n-pentyl, 3'-n-Bu, 3'-n-hexyl, 3'-n-cyclopentyl, 3'-n-cyclohexyl, 3'-NHSO₂(4-tBu)Ph, 3'-Me, 3-F, 3-CF₃, 4-NHSO₂(4-tBu)Ph, 4-OH and 4-t-Bu, and wherein Y is selected from the group consisting of H, 4-OH 4-t-Bu, and 3'-NHSO₂(4-tBu)Ph; $R_5$ is selected from the group consisting of O, NH and CH₂; and $R_6$ is selected from the group consisting of (un)substituted aryl, (un)substituted heterocyclic, (un)substituted heteroaromatic, Ar—NHSO₂Ar, Ar—NHCOAr, H, Ph, Me, —CH₂-(4-Cl)Ph, —CH₂CHCH₂, —CH₂OH, CH₂COOH, CH₂OCH₂CHCH₂, —SO₂(4-O-n-Bu)Ph, —SO₂(4-O-Ph)Ph, —SO₂(4-NHAc)Ph, —SO₂(4-CH₂CH₂CO₂Me)Ph, —SO₂(4-OMe)Ph, —SO₂(4-t-Bu)Ph, and $R_6$—CN. In another aspect, $R_4$ and $R_6$ are covalently linked via.

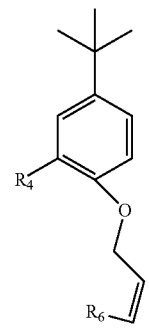

In accordance with a first example, diaryloxindole compounds are represented by Formula I, set forth below.

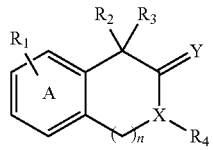

Formula I

In at least certain examples, A is selected from the group consisting of carbocyclic aromatic ring, heterocyclic ring and heteroaromatic ring, $R_1$ is selected from the group consisting of (halo)alky, (un)substituted (alkyl)aryl, halogen, CN, COOH, alkenyl, alkynyl, alkoxy and cycloalkoxy, $R_2$ is selected from the group consisting of (un)substituted aryl, (un)substituted heterocyclic, (un)substituted heteroaromatic, Ar—$NHSO_2$Ar and Ar—NHCOAr, $R_3$ is selected from the group consisting of (un)substituted aryl, (un)substituted heterocyclic, (un)substituted heteroaromatic, Ar—$NHSO_2$Ar and Ar—NHCOAr, $R_4$ is selected from the group consisting of (un)substituted aryl, (un)substituted heterocyclic, (un)substituted heteroaromatic, Ar—$NHSO_2$Ar and Ar—NHCOAr, X is selected from the group consisting of unsubstituted or substituted nitrogen, oxygen, sulfur and carbon, Y is selected from the group consisting of unsubstituted or substituted nitrogen, oxygen, sulfur and carbon; and n=0-4.

In accordance with a second example, diaryloxindole compounds are represented by Formula II, set forth below.

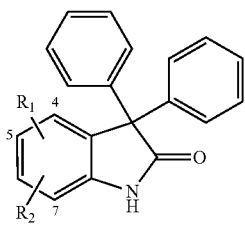

Formula II

In at least certain examples, $R_1$ is selected from the group consisting of H, 5-bromo, 5-chloro, 7-bromo, 5-iodo, 5-$OCF_3$, 5-sulfonic acid, 5-nitro, 4-bromo, 6-bromo, 5-ethyl, 7-ethyl, 4-ethyl, 6-ethyl, 7-iodo, 5-fluoro, 7-COOH and 7-COOMe, and $R_2$ is H. In other examples, $R_1$ is 4-Cl and $R_2$ is selected from the group consisting of 7-formamide-N-[2-(4-Amino-phenyl)-ethyl], 7-COOH, 7-$CH_2$OH and 7-$CH_2$-N-imidazole.

In accordance with a third example, diaryloxindole compounds are represented by Formula III, set forth below.

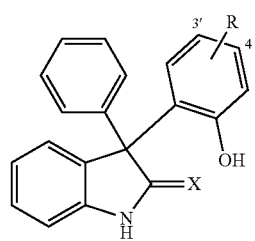

Formula III

In at least certain examples, X is selected from the group consisting of oxygen, NH and $CH_2$, and R is selected from the group consisting of 3'-$CH_2$CH($CO_2$Me)$NH_2$, 3'-$CH_2$CH($CO_2$Me)NHFmoc, 3'-t-Bu, 3'-t-Bu, 3'-OH, 3'-$O(CH_2)_3$CHCH$_2$, 3'-$O(CH_2)_4$Br, 3'-$O(CH_2)_4$NMe$_2$, 3'-$O(CH_2)_4$N$_3$,

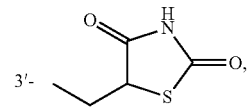

3'-$O(CH_2)_4$NH$_2$, 3'-$CF_3$, 3'-$CH_3$, 3'-n-heptyl, 3'-n-nonyl3'-i-Bu, 3'-i-Propyl, 3'-n-Propyl, 3'-n-Octyl, 3'-Et, 3'-n-pentyl, 3'-n-Bu, 3'-n-Hexyl, 3'-n-cyclopentyl, 3'-n-cyclohexyl, 4-$NHSO_2$(4-tBu)Ph and 3'-$NHSO_2$(4-tBu)Ph.

In accordance with a fourth example, diaryloxindole compounds are represented by Formula IV, set forth below.

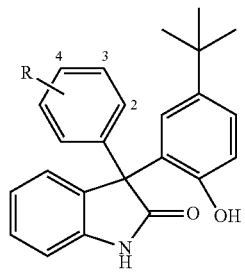

Formula IV

In at least certain examples, R is selected from the group consisting of 4-F, 4-$O(CH_2)_3$CHCH$_2$, 3-Cl, 3-F, 3-Me, 2-Me and 2-OMe.

In accordance with a fifth example, diaryloxindole compounds are represented by Formula V, set forth below.

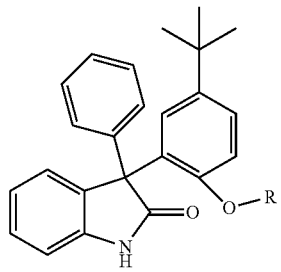

Formula V

In at least certain examples, R is selected from the group consisting of —$SO_2$-camphor, —$CO(CH_2)_6$COOH, —$CO(CH_2)_3$CONHOH, —$CH_2CH_2$NHBoc, —$CO(CH_2)_3$COOH, —$CH_2$COOH, —$CH_2$CO-Leu-Phe-$CH_2$OH and —$CH_2$COOMe.

In accordance with a sixth example, diaryloxindole compounds are represented by Formula VI, set forth below.

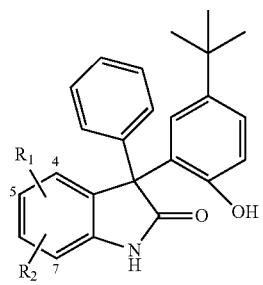

Formula VI

In at least certain examples, $R_1$ is selected from the group consisting of 7-Br, 4-Cl, 5-Br, 5-$NO_2$, 5-I, 5-OMe, 5-Cl, 7-$CF_3$, 5-$NH_2$, 4-Br, 6-Br, H, 7-OMe, 7-I, 5-Et, 7-Et, 4-Et, 6-Et, 5-F, 5-$N_3$, 7-COOH, 4-Cl, 6-Cl and 5-$NHSO_2$-1-napthyl, and $R_2$ is H. In other examples, $R_1$ is 4-Cl and $R_2$ is 7-COOH.

In accordance with a seventh example, diaryloxindole compounds are represented by Formula VII, set forth below.

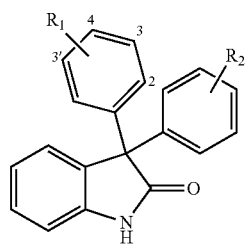

Formula VII

In at least certain examples, $R_1$ is selected from the group consisting of H, 2-OH, 3-O$(CH_2)_4NMe_2$, 3-O$(CH_2)_4N_3$, 3-t-Bu, 2-OMe, 3-OMe, 4-OH, 4-n-propyl, 4-i-Bu, 4-n-Bu, 4-O$(CH_2)_2$OH, 4-OMe, 2-$CH_2CO_2H$ and 4-t-Bu, and $R_2$ is H. In other examples, $R_1$ is selected from the group consisting of 2-OH, 4-OMe, 3-t-Bu, 2-OMe, 2-OH, 4-OH, 4-OPh, 4-Ph and 4-$NMe_2$, and $R_2$ is selected from the group consisting of 2-OH, 4-OH and 4-t-Bu.

In accordance with an eighth example, diaryloxindole compounds are represented by Formula VIII, set forth below.

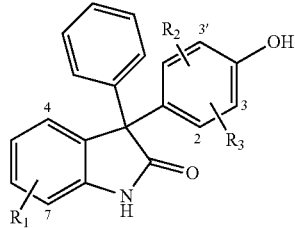

Formula VIII

In at least certain examples, $R_1$ is selected from the group consisting of H and 7-COOH, $R_2$ is selected from a group consisting of H, 2-Me, 3'-Me, 3-F and 3-$CF_3$, and $R_3$ is selected from a group consisting of H, 2-NHFmoc, 2-$NHSO_2CH_2$Ph, 2-$NHSO_2CH_3$, 2-$NHSO_2$(4-tBu)Ph, 2-$NHSO_2$(4-NHAc)Ph, 2-$NHSO_2$(3-$CF_3$)Ph, 2-$NHSO_2$(4-$NO_2$)Ph, 2-$NHSO_2$(4-OMe)Ph, 2-$NHSO_2$(4-Br)Ph, 2-$NHSO_2$(4-I)Ph, 2-$NHSO_2$(4-Ph)Ph, 2-$NHSO_2$(4-OPh)Ph, 2-NHAc, 2-NHCO(4-tBu)Ph and 3-$NHSO_2$(4-tBu)Ph.

In accordance with a ninth example, diaryloxindole compounds are represented by Formula IX, set forth below.

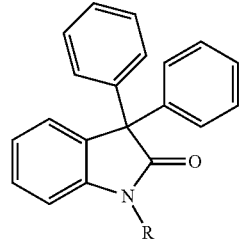

Formula IX

In at least certain examples, R is selected from the group consisting of Ph, Me, —$CH_2$-(4-Cl)Ph, —$CH_2CHCH_2$, —$CH_2$OH, $CH_2$COOH, $CH_2OCH_2CHCH_2$, —$SO_2$(4-O-n-Bu)Ph, —$SO_2$(4-O-Ph)Ph, —$SO_2$(4-NHAc)Ph, —$SO_2$(4-$CH_2CH_2CO_2$Me)Ph, —$SO_2$(4-OMe)Ph and —$SO_2$(4-t-Bu)Ph.

In accordance with a tenth example, diaryloxindole compounds are represented by Formulae X-XII, set forth below.

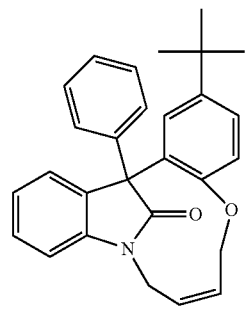

Formula X

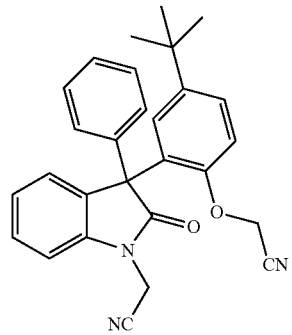

Formula XI

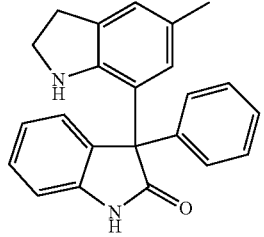

Formula XII

In accordance with an eleventh example, diaryloxindole compounds are represented by Formula XIII, set forth below.

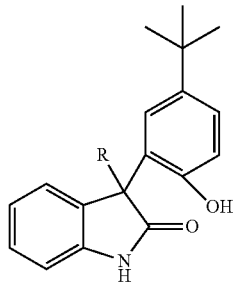

Formula XIII

In at least certain examples, R is selected from the group consisting of 2-thiophene, —(CH$_2$)$_{11}$CH$_3$, —CH$_2$Ph, —CCH, -cyclohexyl and —C$_6$F$_5$ (pentafluorophenyl).

In accordance with a twelfth example, diaryloxindole compounds are represented by Formula XIV, set forth below.

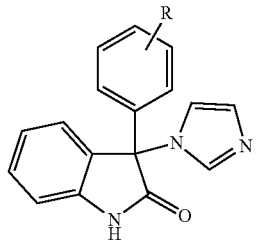

Formula XIV

In at least certain examples, R is selected from the group consisting of H, 3-Cl, 3-F, 3-Me and 3-t-Bu.

Figure 4:
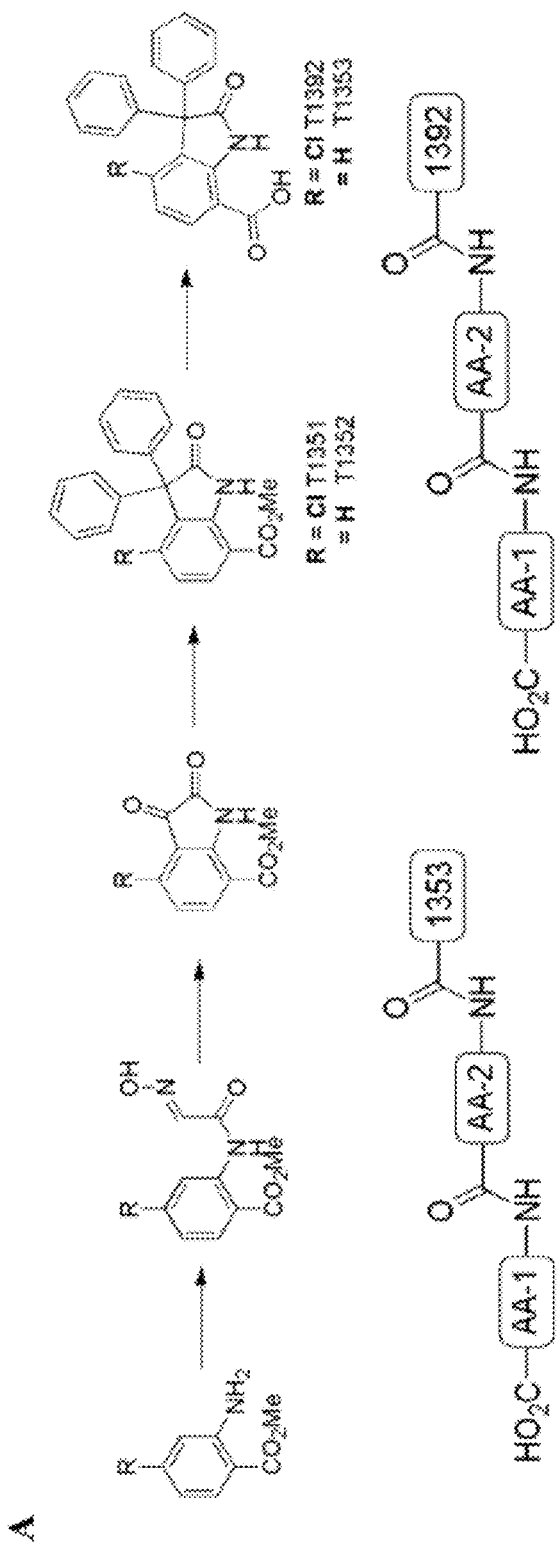
FIGS. 4A-4B depict a general schematic for the synthesis of peptides that contain the diaryloxindole moiety.
Figure 5:
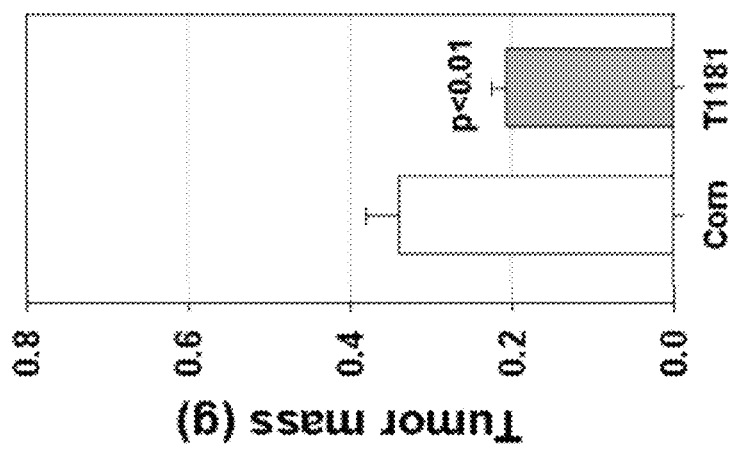
FIG. 5 graphically depicts a decrease in squamous cell carcinoma (KLN) tumor mass from DBA/2 J mice after six weeks of treatment by oral administration with compound 1181 at 320 mg/kg/day.

In accordance with other examples, diaryloxindole compounds include, but are not limited to, compounds comprising Formula I to Formula XIV, and the active and/or partially active compounds set forth in FIGS. 4A-4B and Tables 1-14.

In at least certain examples, the compounds disclosed here can be used in the treatment of cellular proliferative disorders, such as cancer. Treatment of cellular proliferative disorders is intended to include, but is not limited to, inhibition of proliferation including rapid proliferation. As used herein, the term "cellular proliferative disorder" includes, but is not limited to, disorders characterized by undesirable or inappropriate proliferation of one or more subset(s) of cells in a multicellular organism. The term "cancer" refers to various types of malignant neoplasms, most of which can invade surrounding tissues, and may metastasize to different sites (see, for example, PDR Medical Dictionary 1st edition (1995), incorporated herein by reference in its entirety for all purposes). The terms "neoplasm" and "tumor" refer to an abnormal tissue that grows by cellular proliferation more rapidly than normal and continues to grow after the stimuli that initiated proliferation is removed. Id. Such abnormal tissue shows partial or complete lack of structural organization and functional coordination with the normal tissue which may be either benign (i.e., benign tumor) or malignant (i.e., malignant tumor).

The language "treatment of cellular proliferative disorders" is intended to include, but is not limited to, the prevention of the growth of neoplasms in a subject or a reduction in the growth of pre-existing neoplasms in a subject. The inhibition also can be the inhibition of the metastasis of a neoplasm from one site to another. In certain embodiments, the neoplasms are sensitive to one or more diaryloxindole compounds of the present invention. Examples of the types of neoplasms intended to be encompassed by the present invention include, but are not limited to, those neoplasms associated with cancers of the breast, skin, bone, prostate, ovaries, uterus, cervix, liver, lung, brain, larynx, gallbladder, pancreas, rectum, parathyroid, thyroid, adrenal gland, immune system, neural tissue, head and neck, colon, stomach, bronchi, and/or kidneys.

In accordance with certain other examples, methods for treating viral infections are also disclosed. Treatment of viral infections is intended to include, but is not limited to, the use of a diaryloxindole compound described herein to prevent the initiation of viral protein synthesis. The term "viral infection," as used herein, refers to one or more cells which have been infected with a virus, such as a DNA or RNA animal virus. As used herein, RNA viruses include, but are not limited to, virus families such as picornaviridae (e.g., polioviruses), reoviridae (e.g., rotaviruses), togaviridae (e.g., encephalitis viruses, yellow fever virus, rubella virus), orthomyxoviridae (e.g., influenza viruses), paramyxoviridae (e.g., respiratory syncytial virus, measles virus, mumps virus, parainfluenza virus), rhabdoviridae (e.g., rabies virus), coronaviridae, bunyaviridae, flaviviridae, filoviridae, arenaviridae, bunyaviridae, and retroviridae (e.g., human T-cell lymphotropic viruses (HTLV), human immunodeficiency viruses (HIV)). As used herein, DNA viruses include, but are not limited to, virus families such as papovaviridae (e.g., papilloma viruses), adenoviridae (e.g., adenovirus), herpesviridae (e.g., herpes simplex viruses), and poxviridae (e.g., variola viruses). In certain embodiments, the viral infection is caused by hepatitis B virus, hepatitis C virus, and/or HIV.

In accordance with other examples, methods for treating disorders associated with viral infections are disclosed. Treatment of one or more disorders associated with viral infections is intended to include, but is not limited to, the use of a diaryloxindole compound described herein to reduce or alleviate one or more symptoms of a viral infection. As used herein, the term "disorders associated with viral infection" refers to the host's response to infection by one or more viruses. Such responses include, but are not limited to neurological symptoms (e.g., encephalitis, meningoencephalitis, paralysis, myelopathy, neuropathy, aseptic meningitis, hemiparesis, dementia, dysphagia, lack of muscular coordination, impaired vision, coma, and the like), wasting symptoms (e.g., inflammatory cell infiltration, perivascular cuffing of blood vessels, demyelination, necrosis, reactive gliosis and the like), gastroenteritis symptoms (e.g., diarrhea, vomiting, cramps and the like), hepatitis symptoms (nausea, vomiting, right upper quadrant pain, raised liver enzyme levels (e.g., AST, ALT and the like), jaundice and the like), hemorrhagic fever symptoms (e.g., headache, fever, chills body pains, diarrhea, vomiting, dizziness, confusion, abnormal behavior, pharyngitis, conjunctivitis, red face, red neck, hemorrhage, organ failure and the like), oncogenic symptoms (e.g., sarcomas, leukemias and the like, as well as "rare" malignancies, e.g., Kaposi's sarcoma, oral hairy leukoplasia, lymphomas and the like), immunodeficiency symptoms (e.g., opportunistic infections, wasting, rare malignancies, neurological disease, fever, diarrhea, skin rashes and the like), lesions (e.g., warts (e.g., common wart, flat wart, deep hyperkaratotic palmoplantar wart, superficial mosaic type palmoplantar wart and the like), epidermodysplasia, mucosal lesions, ulcers and the like), and systemic symptoms (e.g., fever, chills, headache, muscle pain, bone pain, joint pain, pharyngitis, tonsillitis, sinusitis, otitis, bronchitis, pneumonia, bronchopneumonia, nausea, vomiting, increased salivation, rash, macules, lymphadenopothy, arthritis, ulcers, photosensitivity, weight loss, irritability, restlessness, anxiety, coma, death and the like). Disorders associated with viral infections are described in *Fields Virology* 4th Ed. (2001) Lippincott, Williams & Wilkins, and the introduction to medical virology website (web.uct.ac.za/depts./mmi/jmoodie/introvi2.html), incorporated herein by reference in their entirety for all purposes.

In accordance with other examples, methods for treating non-proliferative, degenerative disorders associated with aberrant translation initiation using a diaryloxindole compound described herein to alleviate and/or reduce one or more symptoms associated with a non-proliferative, degenerative disorder are disclosed. Treatment of non-proliferative, degenerative diseases is intended to include, but is not limited to, the use of diaryloxindole compounds. As used herein, the term "non-proliferative degenerative disorder" is intended to include, but is not limited to, diseases characterized by a loss of function of cells, tissues, and/or organs due to aberrant translation initiation. Non-proliferative degenerative disorders include, but are not limited to, disorders such as Alzheimer's disease and insulin resistance.

The term "calcium releaser," as used herein, refers to molecules which cause a sustained depletion of intracellular $Ca^{2+}$ stores and inhibit translation initiation. Calcium releasers include, but are not limited to, molecules such as clotrimazole (CLT), fatty acids such as EPA, diaryloxindole compounds of the present invention (including, but not limited to compounds comprising Formula I to Formula XIV and the active and/or partially active compounds set forth in FIGS. 4A-4B and Tables 1-14), and the like.

In accordance with certain other examples, kits for treating one or more (1) proliferative disorders, (2) non-proliferative, degenerative disorders, (3) viral infections, and/or (4) disorders associated with viral infections are provided. In one example, the kit may comprise one or more diaryloxindole compounds, or a combination of one or more diaryloxindole compounds. In another example, the kit may comprise a pharmaceutically acceptable carrier. In an additional example, the kit may also include instructions for treating (1) proliferative disorders, (2) non-proliferative, degenerative disorders, (3) viral infections, and/or (4) disorders associated with viral infections. In some examples, the kit may also comprise, e.g., a buffering agent, a preservative, or a protein stabilizing agent. In other examples, the kit may also contain a control sample or a series of control samples which can be assayed and compared to the test sample contained. Other suitable components for including in the kit will be selected by the person of ordinary skill in the art, given the benefit of this disclosure.

In accordance with certain examples, diaryloxindole compounds can be incorporated into pharmaceutical compositions suitable for administration. Such compositions typically comprise the compounds disclosed here and a pharmaceutically acceptable carrier. As used herein the term "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

In accordance with certain examples, a pharmaceutical composition of the invention is formulated to be compatible with its intended route of administration. Such pharmaceutical compositions may be administered by inhalation, transdermally, orally, rectally, transmucosally, intestinally, parenterally, intramuscularly, subcutaneously, intravenously or other suitable methods that will be readily selected by the person of ordinary skill in the art, given the benefit of this disclosure. For example, solutions or suspensions used for parenteral, intradermal, or subcutaneous application can include the following components: a sterile diluent such as water for injection, saline solution, fixed oils, polyethylene glycols, glycerin, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampules, disposable syringes or multiple dose vials made of glass or plastic.

In accordance with other examples, pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, CREMPHOR EL™ (BASF, Parsippany, N.J.), or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

In accordance with other examples, sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, methods of preparation can be vacuum drying and freeze-drying which yields a powder of the active ingredient plus any additional desired ingredient from a previously sterile-filtered solution thereof. Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

In at least certain examples, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These may be prepared according to methods known to those skilled in the art, for example, as described in U.S. Pat. No. 4,522,811, incorporated herein by reference in its entirety for all purposes.

In accordance with certain examples, pharmaceutical compositions of the invention comprise one or more diaryloxindole compounds covalently linked to a peptide (i.e., a polypeptide comprising two or more amino acids) (FIGS. 4A-4B). Peptides may be assembled sequentially from individual amino acids or by linking suitable small peptide fragments. In sequential assembly, the peptide chain is extended stepwise, starting at the C-terminus, by one amino acid per step. In fragment coupling, fragments of different lengths can be linked together, and the fragments can also be obtained by sequential assembly from amino acids or by fragment coupling of still shorter peptides.

In both sequential assembly and fragment coupling it is necessary to link the units (e.g., amino acids, peptides, compounds and the like) by forming an amide linkage, which can be accomplished via a variety of enzymatic and chemical methods. The methods described herein for formation of peptidic amide linkages are also suitable for the formation of non-peptidic amide linkages.

Chemical methods for forming the amide linkage are described in detail in standard references on peptide chemistry, including Muller, *Methoden der organischen Chemie* Vol. XV/2, 1-364, Thieme Verlag, Stuttgart, (1974); Stewart and Young, *Solid Phase Peptide Synthesis,* 31-34 and 71-82, Pierce Chemical Company, Rockford, Ill. (1984); Bodanszky et al., *Peptide Synthesis,* 85-128, John Wiley & Sons, New York, (1976); *Practice of Peptide Synthesis,* M. Bodansky, A. Bodansky, Springer-Verlag, 1994 and other standard works in peptide chemistry, incorporated herein by reference in their entirety for all purposes. Methods include the azide method, the symmetric and mixed anhydride method, the use of in situ generated or preformed active esters, the use of urethane protected N-carboxy anhydrides of amino acids and the formation of the amide linkage using coupling reagents, such as dicyclohexylcarbodiimide (DCC), diisopropylcarbodiimide (DIC), 1-ethoxycarbonyl-2-ethoxy-1,2-dihydroquinoline (EEDQ), pivaloyl chloride, 1-ethyl-3-(3-dimethylaminopropyl)carbodiimide hydrochloride (EDCI), n-propane-phosphonic anhydride (PPA), N,N-bis (2-oxo-3-oxazolidinyl) amido phosphoryl chloride (BOP-Cl), bromo-tris-pyrrolidinophosphonium hexafluorophosphate (PyBrop), diphenylphosphoryl azide (DPPA), Castro's reagent (BOP, PyBop), O-benzotriazolyl-N,N,N',N'-tetramethyluronium salts (HBTU), O-azabenzotriazolyl-N,N,N',N'-tetramethyluronuim salts (TATU), diethylphosphoryl cyanide (DEPCN), 2,5-diphenyl-2,3-dihydro-3-oxo-4-hydroxythiophene dioxide (Steglich's reagent; HOTDO), 1,1'-carbonyldiimidazole (CDI) and the like. The coupling reagents can be employed alone or in combination with additives such as N,N-dimethyl-4-aminopyridine (DMAP), N-hydroxy-benzotriazole (HOBt), N-hydroxybenzotriazine (HOOBt), N-hydroxysuccinimide (HOSu), 2-hydroxypyridine and the like.

In accordance with other examples, methods of modulating translation initiation for therapeutic purposes are disclosed. In one example, a method involves contacting a cell with an agent that inhibits translation initiation. An agent that inhibits translation initiation can be any one of the compounds described herein, such as a diaryloxindole compound. In at least certain examples, the compound modulates the depletion of intracellular calcium stores. Methods of modulating translation initiation can be performed in vitro (e.g., by culturing a cell with the agent) or, alternatively, in vivo (e.g., by administering the agent to a subject). Certain examples disclosed herein are directed to methods of treating an individual afflicted with a disease or disorder characterized by aberrant translation initiation. Examples of such disorders are described herein. In one embodiment, the method involves administering an agent (e.g., an agent identified by a screening assay described herein), or combination of agents that inhibits translation initiation. As used herein, an individual afflicted with a disease or disorder is intended to include both human and non-human mammals. Examples of non-human mammals include, but are not limited to, non-human primates, horses, cows, goats, sheep, dogs, cats, mice, rats, hamsters, guinea pigs and the like.

The present invention provides for both prophylactic and therapeutic methods of treating a subject for one or more (1) proliferative disorders, (2) non-proliferative, degenerative disorders, (3) viral infections, and/or (4) disorders associated with viral infection. In one aspect, the invention provides a method for preventing in a subject, a disease or condition associated with one or more (1) proliferative disorders, (2) non-proliferative, degenerative disorders, (3) viral infections, and/or (4) disorders associated with viral infection, by administering, to the subject one or more diaryloxindole compounds described herein to modulate one or more (1) proliferative disorders, (2) non-proliferative, degenerative disorders, (3) viral infections, and/or (4) disorders associated with viral infection. Administration of a prophylactic agent can occur prior to the manifestation of symptoms, such that a disease or disorder is prevented or, alternatively, delayed in its progression.

Another aspect of the invention pertains to therapeutic methods of treating one or more (1) proliferative disorders, (2) non-proliferative, degenerative disorders, (3) viral infections, and/or (4) disorders associated with viral infection for therapeutic purposes. Accordingly, in an exemplary embodiment, a therapeutic method of the invention involves contacting a subject with a diaryloxindole compound that therapeutically treats one or more (1) proliferative disorders, (2) non-proliferative, degenerative disorders, (3) viral infections, and/or (4) disorders associated with viral infection.

One embodiment of the present invention involves a method of treating a translation initiation-associated disease or disorder which includes the step of administering a therapeutically and/or prophylactically effective amount of an agent which inhibits translation initiation to a subject. In another embodiment, a subject is administered a therapeutically and/or prophylactically effective amount that is effective to deplete intracellular calcium stores. As defined herein, a therapeutically and/or prophylactically effective amount of agent (i.e., an effective dosage) ranges from about 0.001 to 30 mg/kg body weight, from about 0.01 to 25 mg/kg body weight, from about 0.1 to 20 mg/kg body weight, from about 1 to 10 mg/kg, from about 2 to 9 mg/kg, from about 3 to 8 mg/kg, from about 4 to 7 mg/kg, or from about 5 to 6 mg/kg body weight. The skilled artisan will appreciate that certain factors may influence the dosage required to effectively treat a subject, including but not limited to the severity of the disease or disorder, previous treatments, the general health and/or age of the subject, and other diseases present. Treatment of a subject with a therapeutically and/or prophylactically effective amount of an inhibitor can include a single treatment or can include a series of treatments. It will also be appreciated that the effective dosage of in used for treatment may increase or decrease over the course of a particular treatment.

Example I

General Synthetic Approach to Generate Diaryloxindole Compounds

The general synthetic approaches to produce the diaryloxindole compounds of the present invention are set forth in Tables 1-14. Tables 1-14 depict biological data of compounds synthesized describing the general synthetic strategy for the scaffold set forth at the top of each table. The appropriate isatins were either commercially available or synthesized starting from appropriate anilines.

A bioassay guided iterative approach was taken for the synthesis of the diaryloxindole compounds. The iterative approach involved an initial selection of compounds which were subjected to one or more bioassays, such as those described in Example III. Additional compounds were then synthesized based on bioassay and/or structural (e.g., electronic and steric nature of various diaryloxindole compound substituents) data. The compounds synthesized addressed the electronics and the sterics by substituting the three phenyl rings and the nitrogen with various functional groups. The symmetric diphenyl compounds were obtained using triflic acid (TfOH) following previously reported procedures (Klumpp et al. (1998) *J. Org. Chem.,* 63:4481, incorporated herein by reference in its entirety for all purposes), while the unsymmetrical compounds were synthesized using a two step procedure. The first step involved a Grignard addition to isatin using appropriately substituted starting materials, and the key second step involved the generation of a quaternary center at the three position of the oxindole ring. This was accomplished by an acid catalyzed Friedel-Crafts type condensation of step B with the appropriate aromatic ring to generate diaryloxindoles (Hewawasam et al. (2002) *Bioorganic & Medicinal Chemistry Letters,* 12:1023, incorporated herein by reference in its entirety for all purposes). For activated ring systems that contained an electron-donating group, p-toluene sulfonic acid in dichloroethane allowed the condensation to occur smoothly, while the unactivated ring systems required the use of triflic acid, which is much stronger than p-toluene sulfonic acid.

As a non-limiting example, compounds 1272 and 1273 (set forth in Table 1) were synthesized starting from 3-bromoaniline, which upon condensation with hydroxylamine and chloral hydrate followed by concentrated sulfuric acid yielded an inseparable regioisomeric mixture of 4- and 6-bromo isatins. The addition of the two phenyl groups to the three position of the oxindole allowed easy chromatographic separation of the 4- and 6-bromo-3,3-diphenyloxindoles 1272 and 1273. Table 1 sets forth biological data for diaryloxindole compounds including, but not limited to 1272 and 1273. For Tables 1-14, $Ca^{2+}$ refers to $Ca^{2+}$ release from intracellular stores where a "+" denotes release and a "+/−" denotes inconclusive; eIF2α-P refers to phosphorylation of eIF2α measured by Western blot; SRB refers to the inhibitory concentration to reduce cell growth by 50% ($IC_{50}$) for growth inhibition of A549 lung cancer cells; and n.d. is not determined.

TABLE 1

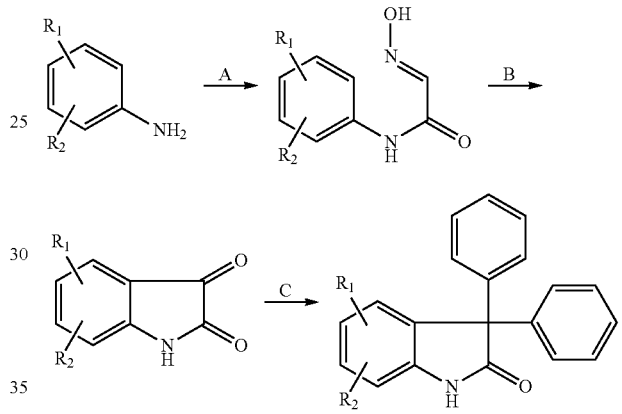

A) Chloral hydrate; $NH_2OH \cdot HCl$; HCl B) $H_2SO_4$ C) TfOH, $C_6H_6$

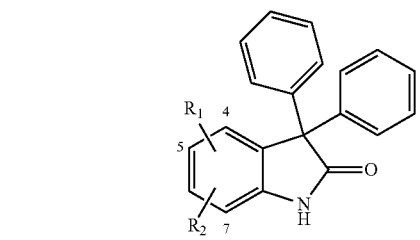

| Compound | $R_1$ | $R_2$ | $Ca^{2+}$ | eIF2α-P | SRB |
|---|---|---|---|---|---|
| 1205 | 5-Br | H | + | 2.05 | 9 |
| 1206 | 5-Cl | H | + | 1.58 | 9 |
| 1207 | 7-Br | H | +/− | 2.01 | 3 |
| 1263 | 5-OCF$_3$ | H | + | n.d. | 8 |
| 1264 | 5-I | H | + | 2.53 | 9 |
| 1265 | 5-NO$_2$ | H | +/− | 2.35 | 14 |
| 1266 | 5-SO$_3$H | H | − | 1.62 | 9 |
| 1267 | 7-I | H | − | 1.88 | 20 |
| 1268 | 7-Et | H | − | 2.19 | 14 |
| 1269 | 5-Et | H | + | 1.64 | >20 |
| 1270 | 4-Et | H | + | 1.68 | >20 |
| 1271 | 6-Et | H | + | 1.58 | 4 |
| 1272 | 4-Br | H | + | 1.63 | 8 |
| 1273 | 6-Br | H | + | 1.72 | 6 |
| 1350 | 5-F | H | + | 1.16 | 9 |
| 1351 | 4-Cl | 7-CO$_2$Me | +/− | 1.35 | >20 |
| 1353 | 7-CO$_2$H | H | − | 1.54 | >20 |

TABLE 1-continued

| | | | | | |
|---|---|---|---|---|---|
| 1354 | 7-CO$_2$Me | H | + | 1.74 | >20 |
| 1355 | 4-Cl | 7- 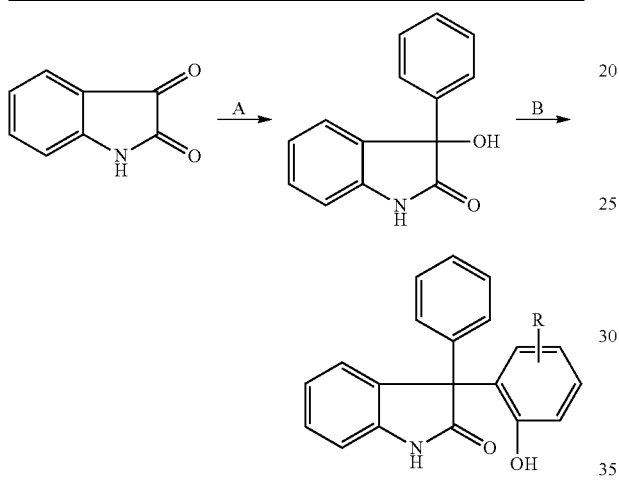 | +/− | 3.80 | 5 |
| 1392 | 4-Cl | 7-CO$_2$H | + | 2.76 | 4 |
| 1398 | 4-Cl | 7-CH$_2$OH | − | 1.48 | 14 |
| 1401 | 4-Cl | 7-CH$_2$(N-Imidazole) | +/− | 2.56 | >20 |

TABLE 2

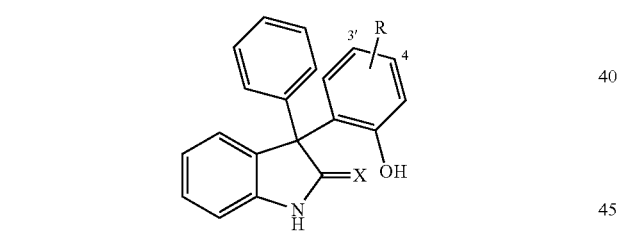

A) PhMgBr B) H$^+$; Substituted Phenol

| Compound | R | X | Ca$^{2+}$ | eIF2α-P | SRB |
|---|---|---|---|---|---|
| 1171 | 3'-CH$_2$CH(CO$_2$Me)NH$_2$ | O | + | n.d | n.d. |
| 1172 | 3'-CH$_2$CH(CO$_2$Me)NHFmoc | O | + | 1.94 | n.d. |
| 1181 | 3'-t-Bu | O | + | 5 | 3 |
| 1182 | 3'-t-Bu | H$_2$ | + | n.d. | 12 |
| 1201 | 3'-OH | O | + | n.d. | 20 |
| 1202 | 3'-O(CH$_2$)$_3$CHCH$_2$ | O | + | n.d. | 6 |
| 1203 | 3'-O(CH$_2$)$_4$Br | O | + | n.d. | 8 |
| 1216 | 3'-O(CH$_2$)$_4$NMe$_2$ | O | +/− | n.d. | >20 |
| 1219 | 3'-O(CH$_2$)$_4$N$_3$ | O | + | n.d. | 5 |
| 1220 | 3'- 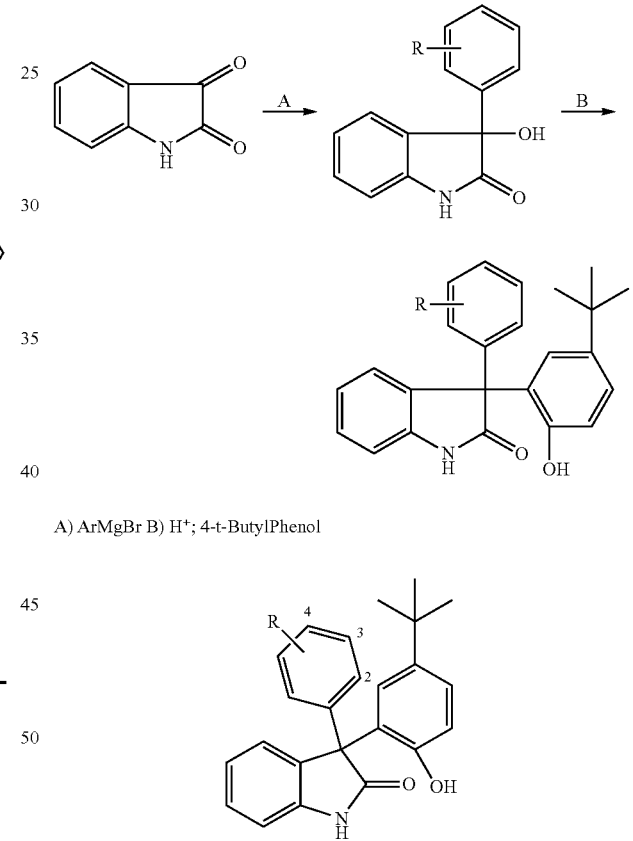 | O | +/− | n.d. | 16 |
| 1228 | 3'-O(CH$_2$)$_4$NH$_2$ | O | + | n.d. | 5 |
| 1243 | 3'-CF$_3$ | O | − | n.d. | >20 |
| 1278 | 3'-CH$_3$ | O | + | 3.33 | 8 |
| 1279 | 3'-n-heptyl | O | +/− | 3.49 | 3 |
| 1280 | 3'-n-nonyl | O | +/− | 3.89 | 3 |

TABLE 2-continued

| | | | | | |
|---|---|---|---|---|---|
| 1281 | 3'-i-Bu | O | + | 7.94 | 3 |
| 1282 | 3'-i-Propyl | O | + | 4.96 | 4 |
| 1283 | 3'-n-Propyl | O | + | 7.67 | 3 |
| 1284 | 3'-n-Octyl | O | − | 2.91 | 3 |
| 1285 | 3'-Et | O | + | 2.96 | 8 |
| 1286 | 3'-n-pentyl | O | + | 8.60 | 3 |
| 1287 | 3'-n-Bu | O | + | 10.08 | 3 |
| 1288 | 3'-n-Hexyl | O | + | 6.28 | 3 |
| 1289 | 3'-n-cyclopentyl | O | + | 6.49 | 3 |
| 1290 | 3'-n-cyclohexyl | O | +/− | 8.60 | 3 |
| 1624 | 4-NHSO$_2$(4-tBu)Ph | O | + | n.d. | <1 |
| 1638 | 3'-NHSO$_2$(4-tBu)Ph | O | + | n.d. | 3 |

TABLE 3

A) ArMgBr B) H$^+$; 4-t-ButylPhenol

| Compound | R | Ca$^{2+}$ | eIF2α-P | SRB |
|---|---|---|---|---|
| 1210 | 4-F | + | 1.86 | 4 |
| 1218 | 4-O(CH$_2$)$_3$CHCH$_2$ | − | 1.36 | 7 |
| 1221 | 3-Cl | + | 3.24 | 3 |
| 1223 | 3-F | + | 4.41 | 7 |
| 1224 | 3-Me | + | 1.74 | 9 |
| 1225 | 2-Me | + | 1.69 | 4 |
| 1226 | 2-OMe | + | 2.22 | 3 |

TABLE 4

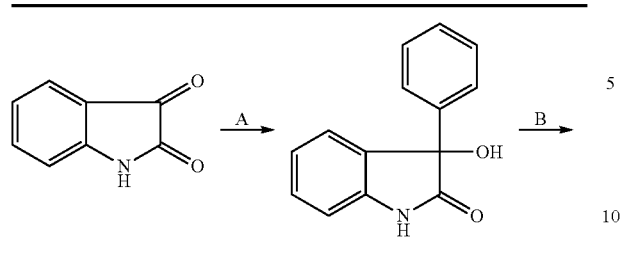

A) PhMgBr B) H+; 4-t-ButylPhenyl substituted ether

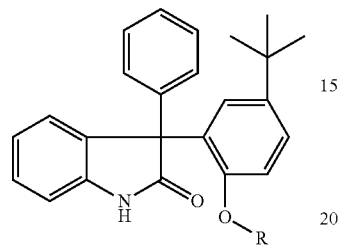

| Compound | R | Ca²⁺ | eIF2α-P | SRB |
|---|---|---|---|---|
| 1319 | —SO₂-Camphor | + | n.d. | 2 |
| 1321 | —CO(CH₂)₆COOH | + | n.d. | 16 |
| 1323 | —CO(CH₂)₃CONHOH | + | n.d. | 3 |
| 1329 | —CH₂CH₂NHBoc | − | 0.89 | 3 |
| 1396 | —CO(CH₂)₃COOH | − | 1.72 | 7 |
| 1397 | —CH₂COOH | + | 1.46 | 8 |
| 1400 | —CH₂CO-Leu-Phe-CH₂OH | + | 3.70 | 3 |
| 1402 | —CH₂CO₂Me | + | 3.94 | 9 |

TABLE 5

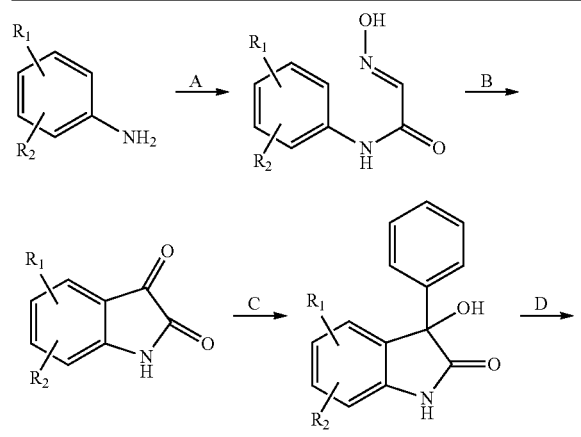

A) Chloral hydrate; NH₂OH•HCl; HCl B) H₂SO₄ C) PhMgBr
D) H+; 4-t-ButylPhenol

TABLE 5-continued

| Compound | R₁ | R₂ | Ca²⁺ | eIF2α-P | SRB |
|---|---|---|---|---|---|
| 1196 | H | 7-Br | + | n.d. | 3 |
| 1209 | H | 4-Cl | + | 2.08 | 8 |
| 1211 | H | 5-Br | + | 1.14 | 3 |
| 1212 | H | 5-NO₂ | + | 1.28 | 4 |
| 1213 | H | 5-I | +/− | 2 | 3 |
| 1214 | H | 5-OMe | + | 1.62 | 6 |
| 1215 | H | 5-Cl | +/− | 1.1 | 3 |
| 1230 | H | 7-CF₃ | +/− | 0.41 | 3 |
| 1231 | H | 5-NH₂ | + | 1.46 | 14 |
| 1234 | H | 4-Br | + | 2.57 | 6 |
| 1235 | H | 6-Br | + | 3.2 | 4 |
| 1238 | 5-NHSO₂-1-napthyl | H | +/− | n.d. | 3 |
| 1240 | H | 7-OMe | + | 1.04 | 8 |
| 1253 | H | 7-I | + | 2.05 | 6 |
| 1254 | H | 5-Et | + | 2.12 | 4 |
| 1256 | H | 7-Et | + | 1.3 | 3 |
| 1257 | H | 4-Et | + | 1.11 | 10 |
| 1258 | H | 6-Et | + | 3.13 | 4 |
| 1312 | H | 5-F | + | n.d. | 4 |
| 1348 | H | 5-N₃ | + | n.d. | 3 |
| 1408 | H | 7-COOH | + | 2.08 | >20 |
| 1418 | 4-Cl | 7-COOH | + | 7.47 | 16 |
| 1428 | H | 4-Cl | + | n.d. | 3 |
| 1429 | H | 6-Cl | + | n.d. | 3 |

TABLE 6

| Compound | R₁ | R₂ | Ca²⁺ | eIF2α-P | SRB |
|---|---|---|---|---|---|
| 1162 | Me | Me | + | n.d. | 5 |
| 1163 | 2-OH; 4-OMe | 2-OH; 4-OMe | + | n.d. | 10 |

TABLE 6-continued

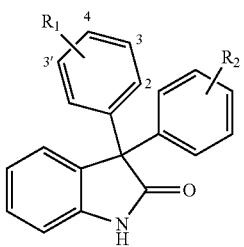

| Compound | R₁ | R₂ | Ca²⁺ | eIF2α-P | SRB |
|---|---|---|---|---|---|
| 1194 | H | H | + | 2.5 | 13 |
| 1195 | 2-OH; 3'-t-Bu | 2-OH; 3'-t-Bu | + | n.d. | 3 |
| 1197 | 2-OH | H | + | 1.50 | 14 |
| 1199 | 2-OH; 3-O(CH₂)₄NMe₂ | H | + | n.d. | >20 |
| 1200 | 2-OH; 3-O(CH₂)₄N₃ | H | + | n.d. | 3 |
| 1208 | 4-Cl | 2-OH | + | 1.42 | 10 |
| 1217 | 3-t-Bu | H | + | 1.5 | 4 |
| 1232 | 3-t-Bu | 4-OH | + | n.d. | 4 |
| 1237 | 2-OMe | 4-t-Bu | + | 1.3 | 17 |
| 1239 | 2-OH | 4-t-Bu | + | 1.88 | 8 |
| 1240 | 4-OH | 4-t-Bu | + | 1.04 | 14 |
| 1259 | 4-OH | 4-OH | − | n.d. | >20 |
| 1260 | 4-OPh | 4-OH | + | n.d. | 12 |
| 1261 | 4-Ph | 4-OH | + | n.d. | 10 |
| 1262 | 4-NMe₂ | 4-OH | +/− | n.d. | 10 |
| 1292 | 2-OMe | H | +/− | 1.04 | 9 |
| 1293 | 3-OMe | H | +/− | 1.30 | 14 |
| 1294 | 4-OMe | H | − | 1.52 | 10 |
| 1295 | 4-OH | H | + | 1.66 | 16 |
| 1296 | 4-n-propyl | H | + | n.d. | 11 |
| 1297 | 4-i-Bu | H | + | 0.7 | 8 |
| 1298 | 4-n-Bu | H | +/− | 0.45 | 8 |
| 1299 | 4-O(CH₂)₂OH | H | + | 0.71 | 5 |
| 1327 | 4-OMe; 2-CH₂CO₂H | H | n.d. | n.d. | >20 |
| 1349 | 4-t-Bu | H | + | 1.27 | 8 |

TABLE 7-continued

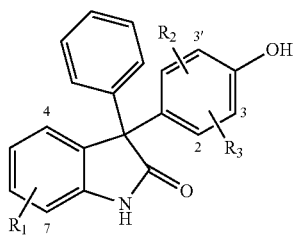

| Compound | R₁ | R₂ | R₃ | Ca²⁺ | eIF2α-P | SRB |
|---|---|---|---|---|---|---|
| 1242 | H | 3-CF₃ | H | + | 2.72 | 14 |
| 1244 | H | 3-F | H | + | 1.38 | 12 |
| 1394 | 7-CO₂H | 3'-Me | 2-NHFmoc | + | 8.21 | 9 |
| 1395 | H | 3'-Me | 2-NHFmoc | − | 1.84 | 3 |
| 1405 | H | 3'-Me | 2-NHSO₂CH₂Ph | + | 1.84 | 4 |
| 1417 | 7-CO₂H | 3'-Me | 2-NHSO₂CH₃ | + | 0.96 | >20 |
| 1427 | H | 3'-Me | 2-NHSO₂CH₃ | + | n.d. | 14 |
| 1430 | H | 3'-Me | 2-NHSO₂(4-tBu)Ph | + | 4.8 | 0.9 |
| 1431 | 7-CO₂H | 3'-Me | 2-NHSO₂(4-tBu)Ph | − | n.d. | >20 |
| 1493 | H | 3'-Me | 2-NHCO(4-tBu)Ph | − | 2.06 | 3 |
| 1512 | H | 3'-Me | 2-NHSO₂(4-NHAc)Ph | + | 1.01 | 4 |
| 1514 | H | 3'-Me | 2-NHSO₂(3-CF₃)Ph | + | 1.65 | 3 |
| 1589 | H | 3'-Me | 2-NHSO₂(4-NO₂)Ph | + | 1 | 5 |
| 1590 | H | 3'-Me | 2-NHSO₂(4-OMe)Ph | + | 1.12 | 5 |
| 1591 | H | 3'-Me | 2-NHSO₂(4-Br)Ph | + | 3.30 | 3 |
| 1592 | H | 3'-Me | 2-NHSO₂(4-I)Ph | + | 5.19 | 3 |
| 1593 | H | 3'-Me | 2-NHSO₂(4-Ph)Ph | − | 2.22 | 4 |
| 1594 | H | 3'-Me | 2-NHSO₂(4-OPh)Ph | − | 3.73 | 5 |
| 1623 | H | H | 2-NHSO₂(4-tBu)Ph | + | n.d. | <1 |
| 1639 | H | 3'-Me | 2-NHAc | n.d. | n.d. | >20 |
| 1648 | H | 2-Me | 3'-NHSO₂(4-tBu)Ph | + | n.d. | n.d. |

TABLE 7

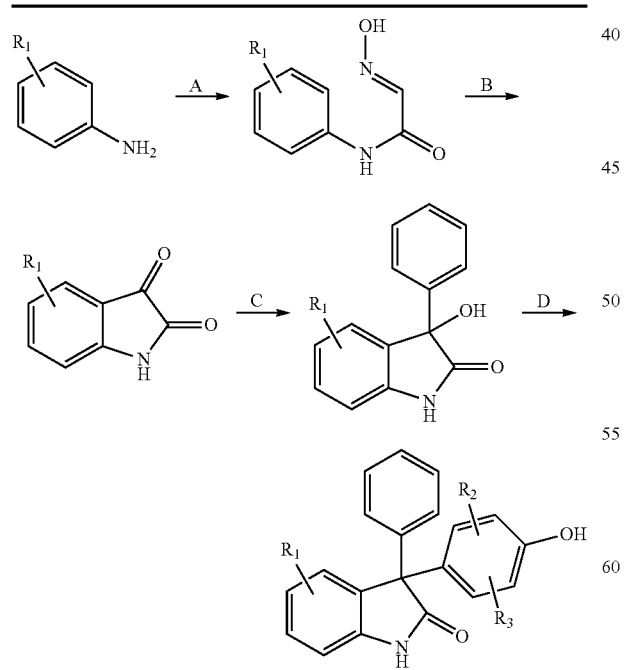

A) Chloral hydrate; NH₂OH•HCl; HCl B) H₂SO₄ C) PhMgBr
D) H⁺; Substituted Phenol

TABLE 8

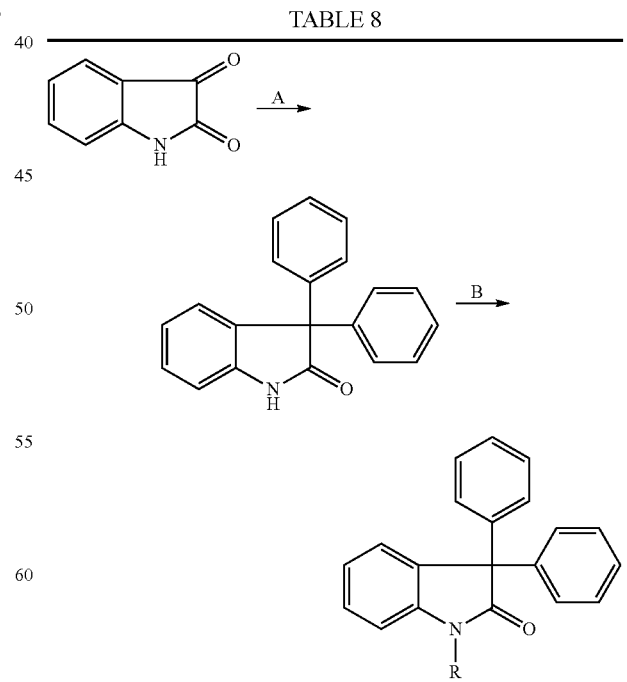

A) TfOH, C₆H₆ B) RX, base

TABLE 8-continued

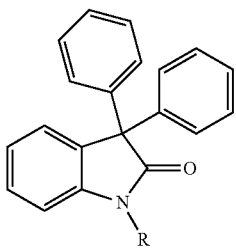

| Compound | R | Ca²⁺ | eIF2α-P | SRB |
|---|---|---|---|---|
| 1300 | Ph | − | n.d. | 8 |
| 1301 | Me | + | n.d. | 20 |
| 1302 | —CH₂—(4-Cl)Ph | − | n.d. | 14 |
| 1303 | —CH₂CHCH₂ | +/− | n.d. | 15 |
| 1304 | —CH₂OH | − | n.d. | 10 |
| 1306 | —SO₂(4-O-n-Bu)Ph | − | n.d. | >20 |
| 1307 | —SO₂(4-O—Ph)Ph | − | n.d. | >20 |
| 1308 | —SO₂(4-NHAc)Ph | − | n.d. | 11 |
| 1309 | —SO₂(4-CH₂CH₂CO₂Me)Ph | − | n.d. | 20 |
| 1310 | —SO₂(4-OMe)Ph | − | n.d. | 20 |
| 1311 | —SO₂(4-t-Bu)Ph | − | n.d. | 11 |

TABLE 9

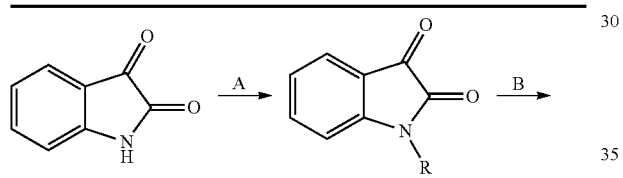

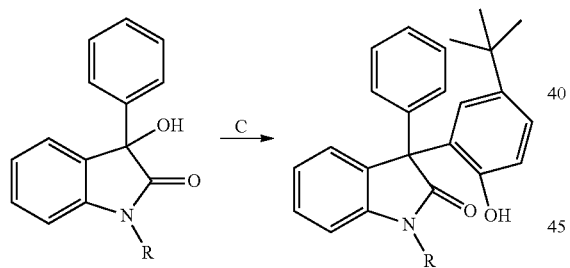

A) RX, base  B) PhMgBr  C) H⁺; 4-t-ButylPhenyl substituted ether

| Compound | R | Ca²⁺ | eIF2α-P | SRB |
|---|---|---|---|---|
| 1227 | —CH₂OCH₂CHCH₂ | + | n.d. | 3 |
| 1236 | —CH₂CHCH₂ | +/− | 2.23 | 3 |
| 1255 | —Ph | − | n.d. | 4 |
| 1339 | —CH₂COOH | − | n.d. | >20 |

TABLE 10

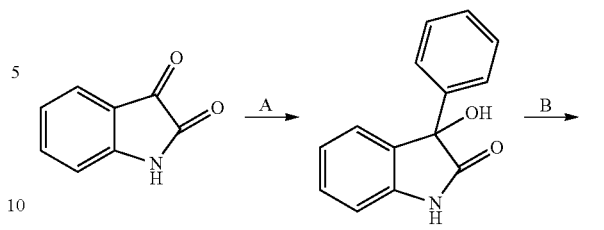

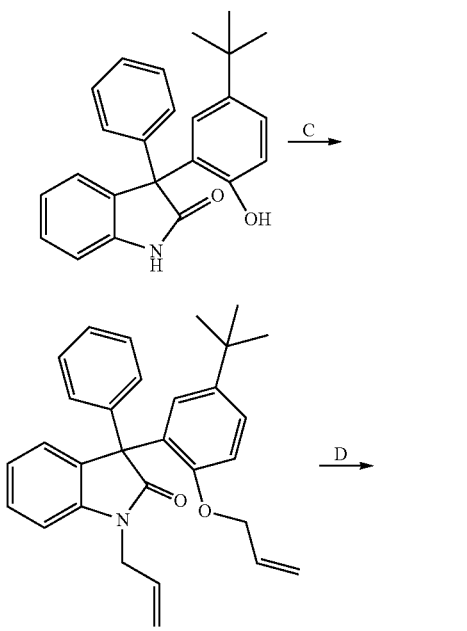

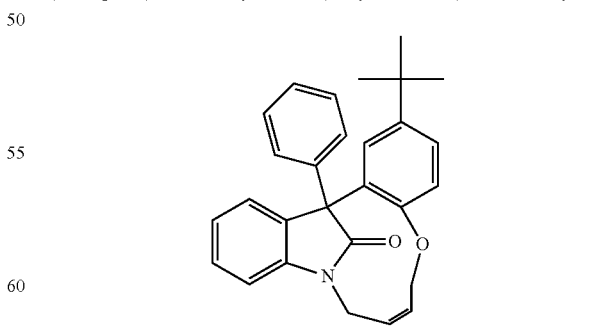

A) PhMgBr  B) H⁺; 4-t-ButylPhenol  C) AllylBromide  D) Grubbs catalyst

| Compound | Ca²⁺ | eIF2α-P | SRB |
|---|---|---|---|
| 1291 | − | n.d. | >20 |

TABLE 11
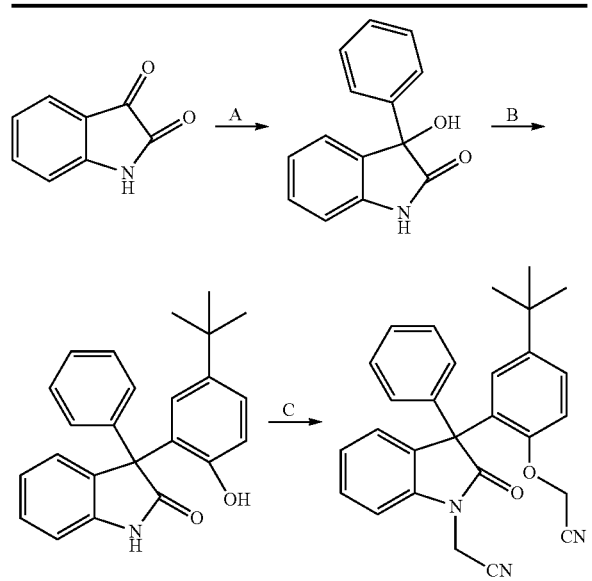
A) PhMgBr B) H⁺; 4-t-ButylPhenol C) Bromoacetonitrile
| Compound | Ca²⁺ | eIF2α-P | SRB |
|---|---|---|---|
| 1320 | − | n.d. | 4 |
TABLE 12
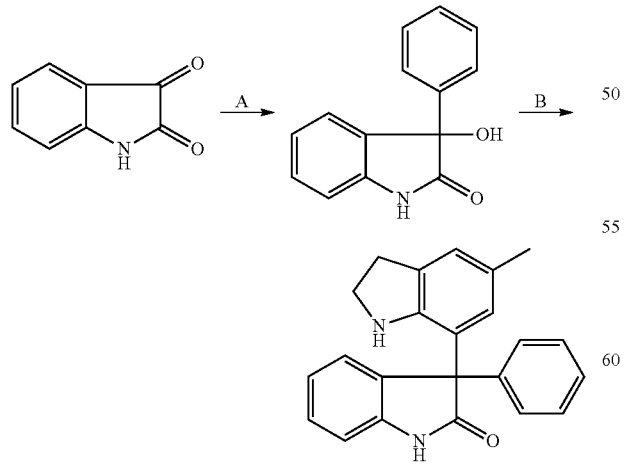
A) TfOH, C₆H₆ B) 5-methylindoline, TfOH
TABLE 12-continued
| Compound | Ca²⁺ | eIF2α-P | SRB |
|---|---|---|---|
| 1313 | + | n.d. | >20 |
TABLE 13
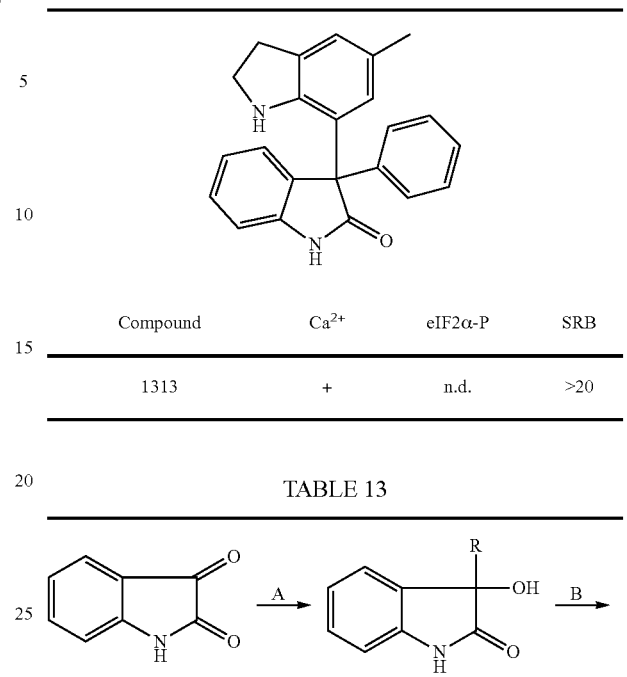
A) RMgBr B) H⁺; 4-t-ButylPhenol
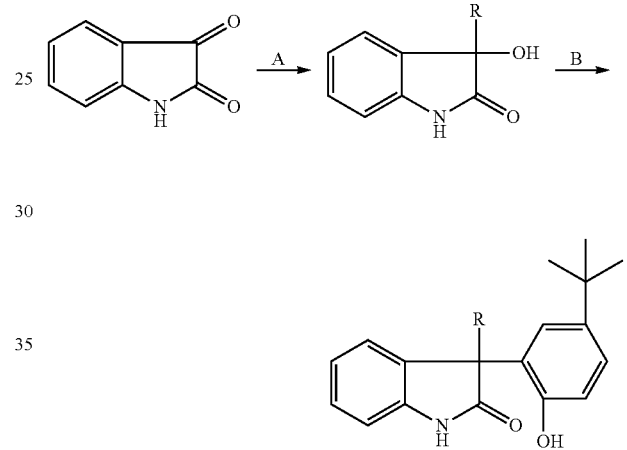
| Compound | R | Ca²⁺ | eIF2α-P | SRB |
|---|---|---|---|---|
| 1222 | 2-Thiophene | + | n.d. | 9 |
| 1274 | —(CH₂)₁₁CH₃ | − | 0.91 | 3 |
| 1275 | —CH₂Ph | +/− | 1.01 | 13 |
| 1276 | —CCH | + | 0.75 | 13 |
| 1277 | -cyclohexyl | − | 1.08 | 10 |
| 1328 | —C₆F₅ | + | n.d. | 3 |

TABLE 14

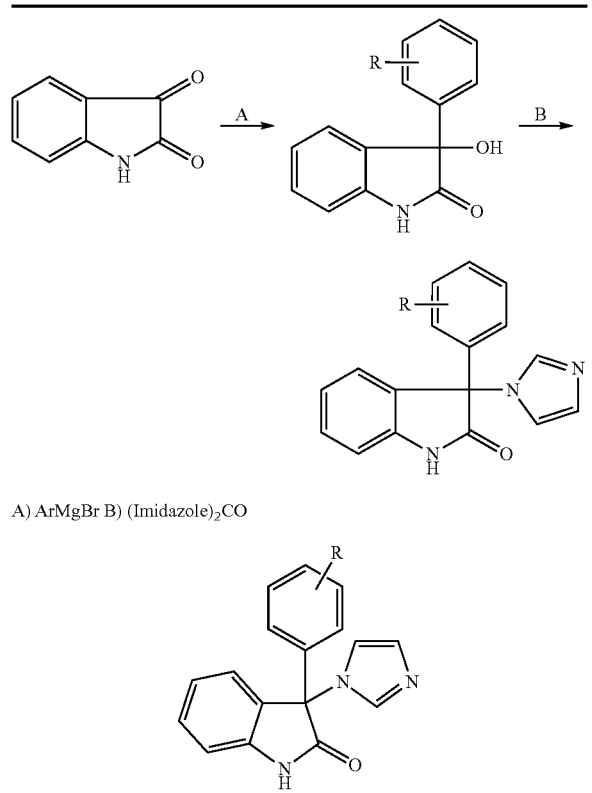

A) ArMgBr  B) (Imidazole)$_2$CO

| Compound | R | Ca$^{2+}$ | eIF2α-P | SRB |
|---|---|---|---|---|
| 1314 | 3-Cl | + | n.d. | >20 |
| 1315 | H | − | n.d. | >20 |
| 1316 | 3-F | − | n.d. | >20 |
| 1317 | 3-Me | − | n.d. | >20 |
| 1318 | 3-t-Bu | + | n.d. | 2 |

Example II

Methods of Synthesizing Intermediate and Final Diaryloxindole Compounds

Compounds described herein were purified either by recrystallization or by column chromatography, and were characterized by $^1$H nuclear magnetic resonance (NMR) and liquid-chromatography-atmospheric pressure chemical ionization-mass spectrometry (LC-APCI-MS).

As a non-limiting example, isatins and substituted isatins (intermediates set forth in Tables 1, 3, 5 and 7) were synthesized by heating a solution of appropriately protected aniline (0.1 moles), chloral hydrate (0.11 moles), hydroxylamine hydrochloride (0.2 moles) in concentrated H$_2$SO$_4$ (12.5 g) and water (700 mL) to 95° C. for ten minutes. The solution was then kept at 4° C. overnight. The cream colored isonitroso intermediate was filtered off, washed with water and dried. This compound was ground to a fine powder in a mortar and pestle, and added, with stirring, in portions over 30 minutes to concentrated H$_2$SO$_4$ (40 g) maintained at 60-65° C. The mixture was then heated at 95° C. for one hour and poured onto ice (300 g). The resulting solid was filtered to give the appropriate substituted isatin.

As another non-limiting example, 3-Aryl-3-hydroxy-substituted-oxindoles (intermediates set forth in tables 2-7 and 9-14) were synthesized by adding dropwise a 1M solution of alkyl or aryl magnesium halide (0.33 mole) to an appropriately substituted isatin (0.1 mole) in 60 mL THF at 0° C. The resulting mixture was allowed to warm to room temperature and let spin at room temperature for twelve hours. The reaction mixture was quenched with a saturated solution of NH$_4$Cl (100 mL) and diluted with 100 mL of dichloromethane. The layers were separated, the organic layer was washed with water followed by brine, dried over Na$_2$SO$_4$ and filtered. The filtrate was concentrated in vacuo to yield the product.

As another non-limiting example, symmetric substituted di-aryloxindoles (final compounds set forth in Tables 1 and 8) were synthesized by adding two mL of substituted benzene to a mixture of appropriately substituted isatins (1 mmol) combined with three mL of freshly distilled triflic acid. The resulting mixture was stirred at room temperature for eight hours. The product mixture was poured over 25 g of ice and extracted into either chloroform or toluene. The organic solution was washed with water and then brine and dried over Na$_2$SO$_4$. Concentration in vacuo yielded the 3,3-diphenyl-substituted oxindoles.

As another non-limiting example, unsymmetrically substituted di-aryloxindoles (final compounds set forth in Tables 2-7 and 9-13) were synthesized by adding freshly distilled triflic acid (1 mmol) in 1 mL dichloromethane to a mixture of appropriately substituted 3-aryl-3-hydroxy-oxindole (0.1 mmol) and appropriately substituted benzene dissolved in 1 mL dichloromethane. The reaction was maintained at room temperature and monitored by thin-layer chromatography (TLC) and liquid chromatography-mass spectrometry (LCMS). Upon completion, the mixture was poured over ice (25 g) and extracted with dichloromethane. The organic layer was dried and concentrated in vacuo to yield the desired product.

As another non-limiting example, unsymmetrically substituted di-aryloxindoles (final compounds set forth in Tables 2-7 and 9-13) were also synthesized by adding p-toluenesulfonic acid (0.3 mmol) in 5 mL dichloromethane to a mixture of appropriately substituted 3-Aryl-3-hydroxy-oxindole (0.1 mmol) and appropriately substituted benzene dissolved in 10 mL dichloroethane. The reaction was heated to 95° C. and monitored by TLC and LCMS, upon completion the reaction mixture was cooled and filtered to remove the p-toluenesulfonic acid. The filtrate was concentrated in vacuo and purified to yield the desired product.

As another non-limiting example, 3-(5-tert-butyl-2-hydroxy-phenyl)-3-phenyl-1,3-dihydro-indol-2-one (compound 1181) was synthesized by adding dropwise a 1M solution of phenylmagnesiumbromide (0.33 mole) to isatin (15 g, 0.1 mole) in 60 mL THF at 0° C. The resulting mixture was allowed to warm to room temperature and let stir at room temperature for 12 hours. The reaction mixture was quenched with a saturated solution of NH$_4$Cl (100 mL) and diluted with 100 mL of dichloromethane. The layers were separated, the organic layer was washed with water followed by brine, dried over Na$_2$SO$_4$, and filtered. The filtrate was concentrated in vacuo to yield 20.1 g (90%) of 3-hydroxy-3-phenyl-1,3-dihydro-indol-2-one. A mixture of the above solid (2.5 g, 10 mmole), p-t-Bu-phenol (1.5 g, 10 mmol), p-toluenesulfonic acid (3 g) in 40 mL dichloroethane, was heated to 95° C. for six hours. The mixture was cooled and filtered. The filtrate was concentrated in vacuo to yield 2.4 g (66%) of the desired product (compound 1181).

As another non-limiting example, 4-tert-butyl-N-[5-hydroxy-4-methyl-2-(2-oxo-3-phenyl-2,3-dihydro-1H-indol-3-yl)-phenyl]-benzenesulfonamide (compound 1430) was synthesized by adding dropwise 4-tert-butyl-benzenesulfonyl chloride (8 g, 34 mmol) in 5 mL dichloromethane to a stirring solution of 5-Amino-2-methyl-phenol (4 g, 32 mmol) in 20 mL pyridine and letting the mixture spin overnight at room temperature. The resulting mixture was concentrated in vacuo and the product was purified by column chromatography to yield 8 g (78%) of 4-tert-butyl-N-(3-hydroxy-4-methyl-phenyl)-benzenesulfonamide. A mixture of 3-hydroxy-3-phenyl-1,3-dihydro-indol-2-one (3.9 g, 17 mmol), 4-tert-butyl-N-(3-hydroxy-4-methyl-phenyl)-benzenesulfonamide (7 g, 22 mmol) and p-toluenesulfonic acid (6.5 g, 32 mmol) in dichloroethane was refluxed for 12 hours. The resulting mixture was cooled to room temperature to yield a colorless solid. The solid was filtered and purified using column chromatography to yield 8 g (88%) of the desired product (compound 1430).

Example III

Analysis of Diaryloxindole Compounds

Without intending to be bound by theory, the mechanism of action of translation initiation inhibitors is set forth in FIG. 1, and includes the depletion (complete or partial depletion) of intracellular calcium ($Ca^{2+}$) stores and phosphorylation of eIF2α. Compounds synthesized using the approaches described herein were screened for their ability to partially deplete intracellular $Ca^{2+}$ stores using FURA-2AM loaded cells (Benzaquen et al. (1995) *Nature Medicine*, 1:534, incorporated herein by reference in its entirety for all purposes). A limited subset of compounds were further screened for their ability to deplete endoplasmic reticulum (ER) $Ca^{2+}$. The $Ca^{2+}$ content of the ER was monitored using ER-targeted, $Ca^{2+}$ sensitive, recombinant proteins. These recombinant proteins emitted light by fluorescent resonance energy transfer (FRET) as a function of the $Ca^{2+}$ content of the medium. Such assays are previously described (Miyawaki, A.; Mizuno, H.; Llopis, J.; Tsien, R. Y.; Jalink, K. *Cameleons as cytosolic and intra-organellar calcium probes*, Oxford University Press: Oxford, London, 2001; pp 3-16, incorporated herein by reference in its entirety for all purposes). Compounds that depleted $Ca^{2+}$ were further evaluated for their ability to phosphorylate eIF2α. eIF2α phosphorylation was measured by Western blot analysis using the phospho-specific anti-eIF2α antibody, as previously described (Aktas et al. (1998) *Proc. Natl. Acad. Sci. USA*, 95:8280, incorporated herein by reference in its entirety for all purposes). Compounds that both depleted ER $Ca^{2+}$ and phosphorylated eIF2α were tested in a lung cancer cell line (A549) for cell growth inhibition as previously described (Palakurthi et al. (2000) *Cancer Research*, 60:2919, incorporated herein by reference in its entirety for all purposes).

Compound 1181 (set forth in Table 2) was determined to be a $Ca^{2+}$ depleting translation initiation inhibitor, as it depleted ER-$Ca^{2+}$, phosphorylated eIF2α, inhibited growth of a cancer cell line (A549), and decreased squamous cell carcinoma tumor mass in mice (FIGS. 2A-2B, 3A-3C and 5). Using compound 1181 for comparison, additional compounds were screened for their ability to inhibit translation initiation in a $Ca^{2+}$ depletion-dependent manner (Tables 1 to 14).

One set of compounds (Table 1) had a variation of the functional groups at the positions $R_1$ and $R_2$ on the oxindole phenyl ring. Substitutions including, but not limited to, 5-Br, 4-Cl, 5-OCF$_3$ and 6-Et groups, resulted in compounds that depleted intracellular $Ca^{2+}$. Compound 1392, which has 4-Cl and 7-CO$_2$H substitutions, showed improved eIF2α phosphorylation, which correlated with improved growth inhibition of cancer cells. Compound 1398 (a negative control) exhibited reduced eIF2α phosphorylation relative to compound 1392, with a concomitant reduced potency of tumor cell growth inhibition.

The positional effect of a bromo group was next investigated by placing a bromo group at 4, 5, 6 and 7 positions on the phenyl ring of the oxindole to generate compounds 1272, 1205, 1273 and 1207, respectively. The 7-substitution abrogated $Ca^{2+}$ depletion activity, and none of the compounds exhibited an increase in eIF2a phosphorylation relative to compound 1392.

Compound 1430 (Table 7) released calcium and showed a 5-fold increase in eIF2α phosphorylation over DMSO at 5 μM. Ternary complex assay was 8-fold over DMSO at 20 μM, and cell growth was inhibited at <1 μM. The plasma levels for this in mice were estimated using liquid chromatography and mass spectrometry (LC-MS). Compound 1430 was orally administered at 160 mg/kg, 240 mg/kg, and 320 mg/kg to DBA/2J mice and the plasma concentration was measured at three time points, one hour, three hours, and six hours, and is set forth in Table 15. The plasma was isolated from the mice by heart-lung puncture and the samples were processed and analyzed by LC-MS. The concentrations at each time and dose are in nmoles/mL of plasma (n.d.=not detected; X=not determined).

TABLE 15

| Time | Dose | | |
| --- | --- | --- | --- |
| | 320 mg/kg | 240 mg/kg | 160 mg/kg |
| 1 hour | 14.0 | 6.8 | 5.7 |
| 3 hours | 3.8 | 4.0 | 3.8 |
| 6 hours | 2.8 | n.d. | X |

Other embodiments will be evident to those of skill in the art. It should be understood that the foregoing description is provided for clarity only and is merely exemplary. The spirit and scope of the present invention are not limited to the above examples, but are encompassed by the following claims. All publications and patent applications cited above are incorporated by reference herein in their entirety for all purposes to the same extent as if each individual publication or patent application were specifically indicated to be so incorporated by reference.

What is claimed is:

1. A method of inhibiting translation initiation in a cell comprising contacting the cell with a compound of formula II, formula IX, X, XI, XII, XIII or XIV wherein
the compound of formula II is:

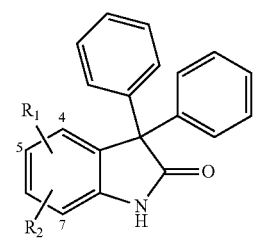

Formula II wherein $R_1$ is selected from the group consisting of H, 5-bromo, 5-chloro, 7-bromo, 5-iodo, 5-OCF$_3$, 5-sulfonic acid, 5-nitro, 4-bromo, 6-bromo, 5-ethyl, 7-ethyl, 4-ethyl, 6-ethyl, 7-iodo, 5-fluoro, 7-COOH, 7-COOMe and 4-Cl; and R₂ is selected from the group consisting of 7-formamide-N-[2-(4-amino-phenyl)-ethyl], 7-CO₂H, 7-CH₂OH, 7-CH₂—N-imidazole and H with the proviso that R₁ and R₂ cannot both be H, and with the further proviso that when R₂ is H, R₁ cannot be 5-chloro, 5-nitro or 5-fluoro;

the compound of formula IX is:

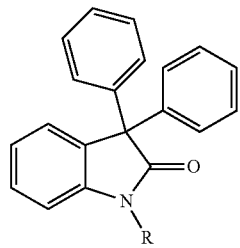

Formula IX wherein R is selected from the group consisting of —CH₂-(4-Cl)Ph, —CH₂CHCH₂, —CH₂OH, —CH₂CO₂H, —CH₂OCH₂CHCH₂, —SO₂(4-O-n-Bu)Ph, —SO₂(4-O-Ph)Ph, —SO₂(4-NHAc)Ph, —SO₂(4-CH₂CH₂CO₂Me)Ph, —SO₂(4-OMe)Ph and —SO₂(4-t-Bu)Ph;

the compound of formula X is:

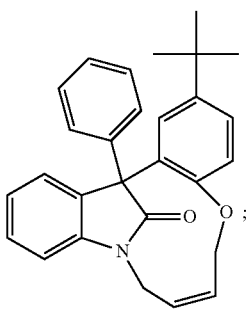

Formula X the compound of formula XI is:

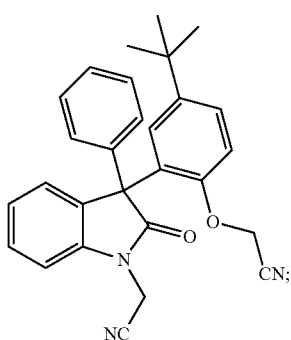

Formula XI the compound of formula XII:

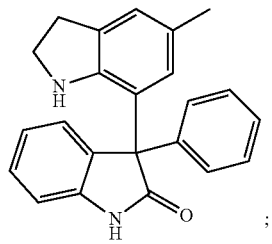

Formula XII the compound of formula XIII:

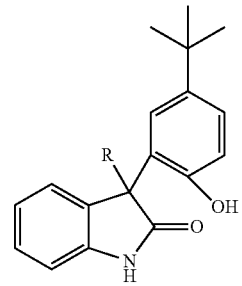

Formula XIII wherein R is selected from the group consisting of 2-Thiophene, —(CH₂)₁₁CH₃, —CH₂Ph, —CCH, -cyclohexyl and —C₆F₅; and the compound of formula XIV is:

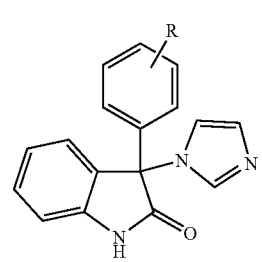

Formula XIV wherein R is selected from the group consisting of H, 3-Cl, 3-F, 3-Me and 3-t-Bu.

2. The method of claim 1, wherein the cell is a cancer cell.

3. The method of claim 1 carried out in an individual by administration of the compound to the individual.

4. The method of claim 3 wherein the compound is administered by inhalation, transdermally, orally, rectally, transmucosally, intestinally, parenterally, intramuscularly, subcutaneously or intravenously.

* * * * *

UNITED STATES PATENT AND TRADEMARK OFFICE
CERTIFICATE OF CORRECTION

| | |
|---|---|
| PATENT NO. | : 8,354,440 B2 |
| APPLICATION NO. | : 13/233074 |
| DATED | : January 15, 2013 |
| INVENTOR(S) | : Halperin et al. |

It is certified that error appears in the above-identified patent and that said Letters Patent is hereby corrected as shown below:

In the Specification

Column 1, under STATEMENT OF GOVERNMENT INTERESTS, Line 20-23:
Please delete "This invention was made with Government support under Grant Number 5 U19 CA87427 awarded by the National Institutes of Health. The Government has certain rights in the invention." and insert --This invention was made with government support under CA087427 awarded by the National Institutes of Health. The government has certain rights in the invention.--

Signed and Sealed this
Twenty-third Day of April, 2024

Katherine Kelly Vidal
*Director of the United States Patent and Trademark Office*